(12) United States Patent
Gurjar et al.

(10) Patent No.: US 7,179,937 B2
(45) Date of Patent: Feb. 20, 2007

(54) CYCLOPENTENONE DERIVATIVES FOR CANCER THERAPY

(75) Inventors: Mukund K. Gurjar, Pune (IN); Radhika D. Wakharkar, Pune (IN); Gautam R. Desiraju, Hyderabad (IN); Ashwini Nangia, Hyderabad (IN); Jhillu Singh Yadav, Hyderabad (IN); Anand C. Burman, Ghaziabad (IN); Rama Mukherjee, Ghaziabad (IN); Hanumant Bapu Rao Borate, Pune (IN); Srivari Chandrasekhar, Hyderabad (IN); Manu Jaggi, Ghaziabad (IN); Anuo T. Singh, Ghaziabad (IN); Kamal Kapoor, Ghaziabad (IN); Sanjay Sarkhel, Hyderabad (IN); K. V. V. M. Sairam, Hyderabad (IN)

(73) Assignee: Dabur Research Foundation (IN)

( * ) Notice: Subject to any disclaimer, the term of this patent is extended or adjusted under 35 U.S.C. 154(b) by 309 days.

(21) Appl. No.: 10/309,754

(22) Filed: Dec. 4, 2002

(65) Prior Publication Data

US 2003/0229146 A1   Dec. 11, 2003

Related U.S. Application Data

(60) Provisional application No. 60/337,711, filed on Dec. 5, 2001.

(51) Int. Cl.
*C07C 61/06* (2006.01)
*C07C 249/00* (2006.01)

(52) U.S. Cl. .................. 562/503; 564/248; 562/504
(58) Field of Classification Search ................ 568/379; 564/248, 253, 254, 255, 267, 271; 562/503, 562/504
See application file for complete search history.

(56) References Cited

OTHER PUBLICATIONS

Challener et al., Journal of the American Chemical Society (1993), 115(4), 1359-76.*
Melchiorre et al. European Journal of Medicinal Chemistry (1975), 10(6), 623-7, Chemical Abstract online citation.*
Shoppee et al. Journal of the Chemical Society, Perkin Transactions 1: Organic and Bio-Organic Chemistry (1972-1999) (1972), (18), 2271-6 Chemical Abstracts online citation.*
Chemical Abstracts online citation [retrieved Mar. 30, 2006] from STN, Columbus, OH, USA, Abstract No. 1951:11128.*

* cited by examiner

*Primary Examiner*—Thurman K. Page
*Assistant Examiner*—Karl Puttlitz
(74) *Attorney, Agent, or Firm*—Ladas & Parry

(57) ABSTRACT

The invention relates to the use of derivatives of cyclopentenone for the inhibition or prevention of the growth or multiplication of cancer cells, and to therapeutic compositions containing such compounds. The invention relates more specifically to the use of derivatives of cyclopentenone for the inhibition and/or prevention of cancer of the colon, pancreas, larynx, ovary, duodenum, kidney, oral cavity, prostate, lung, endothelial cells and leukemias.

41 Claims, 1 Drawing Sheet

CYCLOPENTENONE DERIVATIVES FOR CANCER THERAPY

This application claims the benefit of U.S. Provisional Application(s) No(s).: APPLICATION NO(S).: 60/337,711 FILING DATE Dec. 5, 2001 and incorporates the same by reference.

FIELD OF THE INVENTION

The invention relates to the use of derivatives of cyclopentenone for the inhibition or prevention of the growth or multiplication of cancer cells, and to therapeutic compositions containing such compounds. The invention relates more specifically to the use of derivatives of cyclopentenone for the inhibition and/or prevention of cancer of the colon, pancreas, larynx, ovary, duodenum, kidney, oral cavity, prostate, lung, endothelial cells and leukemias.

BACKGROUND OF THE INVENTION

The treatment of solid-tumor cancers continues to rely on the development of architecturally new and biologically more potent and anti-tumor, antimitotic agents. Vincristine, taxol, dolastatin 10 and combretastatin A-4 (CA-4) prodrugs have established clinical efficacy as antimitotic agents. We have designed (molecular modeling and 3D-QSAR) and synthesized a novel class of compounds viz. cyclopentenone derivatives i.e 2,3-diaryl-4 or 5-substituted cyclopent-2-en-1-one derivatives in particular which could mimic combretastatin A-4. The lead compounds in our designed molecules demonstrate remarkable cytotoxic activity against a variety of human cancer cell lines representing cancer of the colon, pancreas, larynx, ovary, duodenum, kidney, oral cavity, prostate, lung, endothelial cells and leukemias

SUMMARY OF THE INVENTION

This invention relates to novel cyclopentenone derivatives for cancer therapy said derivatives having a general structural formula (1)

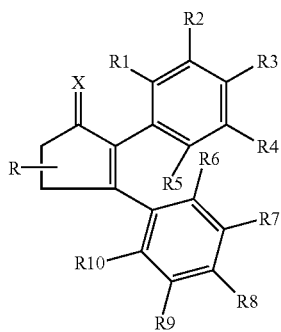

1 wherein X is oxygen, hydroxyimino, alkoxyimino, aryloxyimino or arylimino; R is hydroxy, oxo, amino, alkylamino, hydroxyimino, alkoxyimino, aryloxyimino, alkylcarbonyloxy, aroyloxy, alkoxy, methoxymethyloxy, 2-methoxyethoxymethyloxy, tert.-butyldimethylsilyloxy, trimethylsilyloxy, carboxyl, carboxylate salts, or carboxylic acid esters (preferably $C_1$–$C_4$ alkyl esters); $R_1$ to $R_{10}$ are the same or different and represent hydrogen, hydroxy, alkyl, alkoxy, methoxymethyloxy, 2-methoxyethoxymethyloxy, tert-butyldimethylsilyloxy, trimethylsilyloxy, chloro, fluoro, bromo, mercapto, alkylthio, nitro, amino, monoalkylamino, dialkylamino, azido, carboxyl, carbalkoxy, alkylcarbonyloxy, carboxymethyloxy, $NHCOCH_3$, $NHCOCF_3$, NH-alkyl (preferably, the alkyl of NH-alkyl is methyl, propyl, butyl, or t-butyl), N-dialkyl (the alkyl groups may be the same or different and preferably represent $C_1$–$C_4$ alkyl groups), CN, guanidine, $NHCOOR_{11}$, $CH_2C=NR_{12}R_{13}$; $NHNH_2$, $NHCONH_2$, $NHNHCONH_2$, $NHNHC(=S)NH_2$ and their salts, preferred salts are HCl, and HBr salts; $OPO_3H_2$, $OPO_3Na_2$, $OPO_3K_2$, $SO_2NH_2$, CONH-alkyl (preferably $C_1$–$C_4$), CHO, CH=NOH, or —($CH_2$—$CH_2$—$N[CH_3]$)— fused at $R_8$, $R_9$ positions respectively, methylenedioxy group fused in lieu of either $R_8$, $R_9$ or $R_9$, $R_{10}$ position, respectively, and in the latter $R_8$ is alkoxy (preferably methoxy), and $R_{11}$, $R_{12}$ and $R_{13}$ are lower alkyl groups selected from $C_1$–$C_4$ alkyl groups or a salt thereof.

The present invention also relates to the design and synthesis of novel cyclopentenones derivatives with anticancer activity.

The present invention also provides pharmaceutical compositions of novel derivatives of cyclopentenone based compounds or pharmaceutically acceptable salts of the cyclopentenone based compounds useful for killing or inhibiting multiplication of cancer cells and for testing their bio-activity using cultured human cancer cells as the monitor.

DETAILED DESCRIPTION OF THE INVENTION

Figure 1:
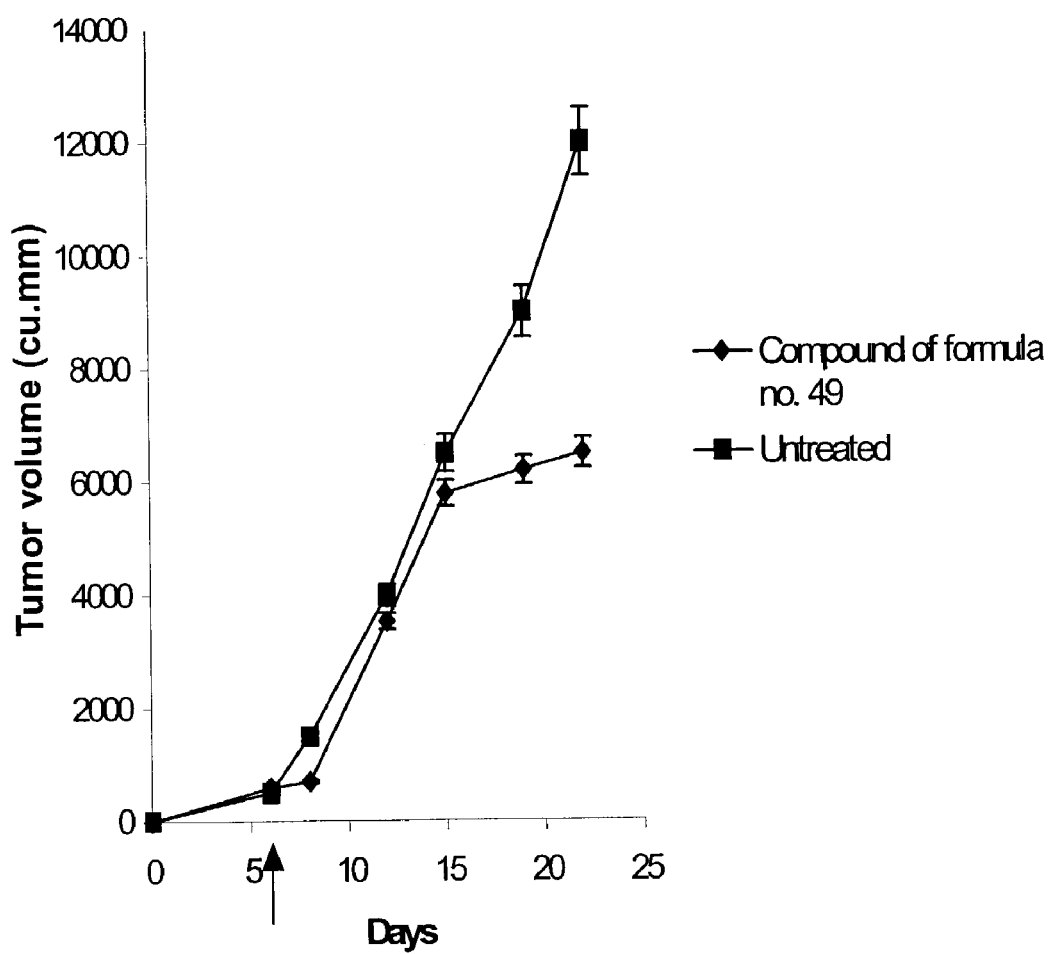
FIG. 1 shows the percent inhibition of the growth of PTC xenograft using the compound of formula no. 49 as compared to the control.

The present invention is directed to the development of cyclopentenone derivatives as new anticancer agents.

As described herein, the present invention encompasses compounds selected from a group of compounds represented by the General formula (1A) and (1B)

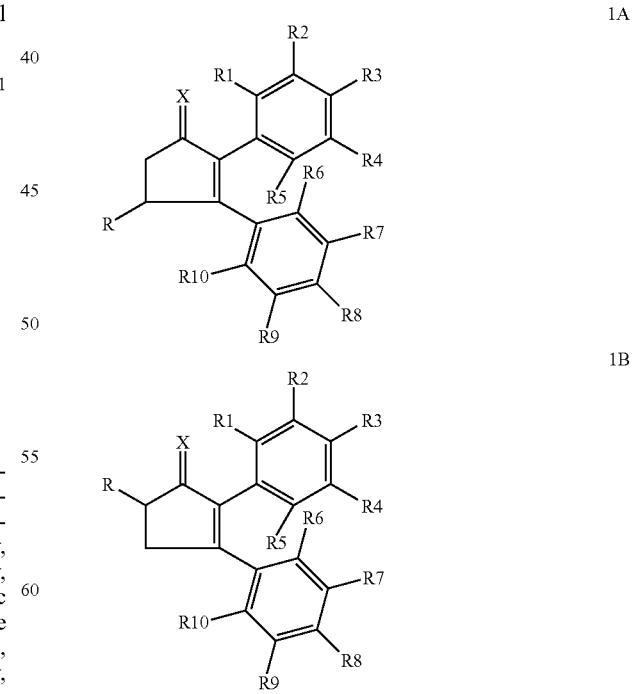

wherein X is oxygen, hydroxyimino, alkoxyimino, aryloxyimino or arylimino; R is hydroxy, oxo, amino, alkylamino, hydroxyimino, alkoxyimino, aryloxyimino, alkylcarbonyloxy, aroyloxy, alkoxy, methoxymethyloxy, 2-methoxyethoxymethyloxy, tert.-butyldimethylsilyloxy, trimethylsilyloxy, carboxyl, carboxylate salts, carboxylic acid esters (preferably $C_1$–$C_4$ alkyl esters); $R_1$ to $R_{10}$ are the same or different and represent hydrogen, hydroxy, alkyl, alkoxy, methoxymethyloxy, 2-methoxyethoxymethyloxy, tert-butyldimethylsilyloxy, trimethylsilyloxy, chloro, fluoro, bromo, mercapto, alkylthio, nitro, amino, monoalkylamino, dialkylamino, azido, carboxyl, alkylcarbonyloxy, carbalkoxy, carboxymethyloxy, $NHCOCH_3$, $NHCOCF_3$, NH-alkyl (preferably, the alkyl of NH-alkyl is methyl, propyl, butyl, t-butyl), N-dialkyl (the alkyl groups may be the same or different and preferably represent $C_1$–$C_4$ alkyl groups), CN, guanidine, $NHCOOR_{11}$, $CH_2C=NR_{12}R_{13}$; $NHNH_2$, $NHCONH_2$, $NHNHCONH_2$, $NHNHC(=S)NH_2$ and their salts (preferred salts are HCl and HBr salts), $OPO_3H_2$, $OPO_3Na_2$, $OPO_3K_2$, $SO_2NH_2$, CONH-alkyl (preferably $C_1$–$C_4$), CHO, or CH=NOH, or —($CH_2$—$CH_2$—N [$CH_3$])— may be fused at $R_8$, $R_9$ positions respectively, methylenedioxy group fused in lieu of either $R_8$, $R_9$ or $R_9$, $R_{10}$ position, respectively, and in the latter $R_8$=alkoxy (preferably methoxy) and $R_{11}$, $R_{12}$ and $R_{13}$ are lower alkyl groups selected from $C_1$–$C_4$ alkyl groups, derivatives and salts thereof.

The present invention is directed to the synthesis of compounds having the structural formula 1

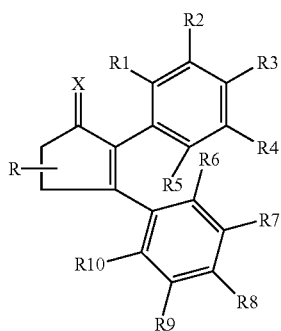

1 having two substituted aryl groups or combinations thereof separated by a bridging unit of C=C which is a part of $C_5$ cyclic unit. The aryl group(s) are preferably substituted by at least one or more alkoxy groups. The preferred substitution pattern is 3,4,5-trimethoxy system in one of the aryl groups.

The present invention contemplates employing compounds of formula 1

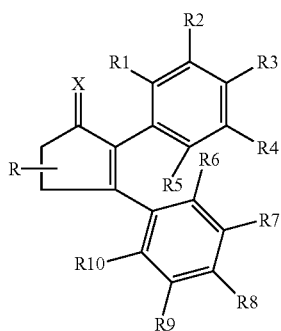

1

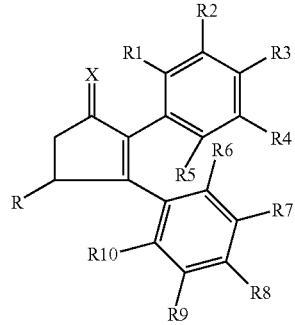

1A

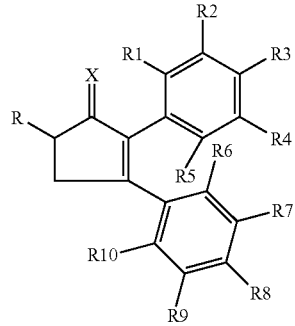

1B having R at C-4 (1A) or C-5 (1B) of the cyclopentenone unit as a free hydroxy group or derivatives thereof.

A preferred compound of the formula 1

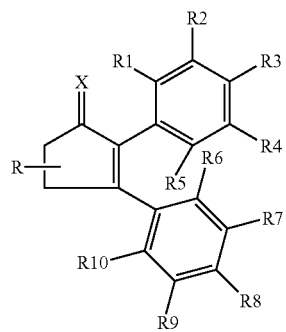

1 wherein X is oxygen or hydroxyimino. Hydroxyimino is expected to provide a more hydrophilic substance required for the biological activity.

As used herein, alkyl is a group having $C_1$–$C_4$ carbon atoms.

As used herein the term alkoxy refers to O-alkyl groups wherein the alkyl group has 1–4 carbon atoms. The preferred alkyl group is methyl.

The aryl group may be phenyl or naphthyl. The aryl group may be substituted. Preferred substituents are hydrogen, hydroxy, alkyl, alkoxy, methoxymethyloxy, 2-methoxyethoxymethyloxy, tert-butyldimethylsilyloxy, trimethylsilyloxy, chloro, fluoro, bromo, mercapto, alkylthio, nitro, amino, alkylamino, dialkylamino, azido, carboxyl, alkylcarbonyloxy, carbalkoxy, carboxymethyloxy, $NHCOCH_3$, NHCOCF$_3$, NH-alkyl (preferably, the alkyl of NH-alkyl is methyl, propyl, butyl, t-butyl), N-dialkyl (the alkyl groups may be the same or different and preferably represent C$_1$–C$_4$ alkyl groups), CN, guanidine, NHCOOR$_{11}$, CH$_2$C=NR$_{12}$R$_{13}$; NHNH$_2$, NHCONH$_2$, NHNHCONH$_2$, NHNHC(=S)NH$_2$ and their salts (preferred salts are HCl and HBr salts); OPO$_3$H$_2$, OPO$_3$Na$_2$, OPO3K$_2$, SO$_2$NH$_2$, CONH-alkyl (preferably C$_1$–C$_4$), CHO, or CH=NOH, or —(CH$_2$—CH$_2$—N[CH$_3$])— may be fused at R$_8$, R$_9$ positions respectively, methylenedioxy group fused at adjacent positions of the aryl ring and R$_{11}$, R$_{12}$ and R$_{13}$ are lower alkyl groups selected from C$_1$–C$_4$ alkyl groups, Alkyl carbonyloxy is a group is the formula O(CO)-alkyl wherein the acyl group ((CO)alkyl) containing 1–4 carbon atoms is bonded to oxygen. The preferred acyl group has 2 carbon atoms.

"Alkylamino", "monoalkylamino" and "dialkylamino" refer to a group wherein one alkyl group or two alkyl groups are bonded to an amino nitrogen, i.e., NH(alkyl) or N(alkyl)$_2$. The NH or N is the bridge connecting the alkyl groups to the aryl/phenyl group of formulae described in this application. Examples include NHMe, NHEt, or N(Me)$_2$, N(Et)$_2$ and the like.

As used herein, alkylthio refers to an S-alkyl wherein the alkylthio is attached as a substituent through the S atom. The S is the bridge connecting the alkyl group to the aryl/phenyl group.

Aryloxyimino includes groups of the formula Ar—O—N= where Ar is aryl.

The "carbalkoxy" is a group wherein the acyl group is bonded to the main aryl/phenyl unit and alkyl is as defined hereinabove. Examples include COOMe, COOEt and the like.

Aroyl is ArCO where Ar is an aryl group. Aroyloxy is ArC(O)O.

Carboxylate salts may be sodium, potassium or ammonium salts. The esters of carboxylic acid may have 1 to 4 carbon atoms in the ester group.

Chemistry

A typical synthesis of 2,3-diaryl-4-hydroxycyclopent-2-en-1-one and 2,3-diaryl-5-hydroxycyclopent-2-en-1-one of General formulae (6A) and (6B) respectively

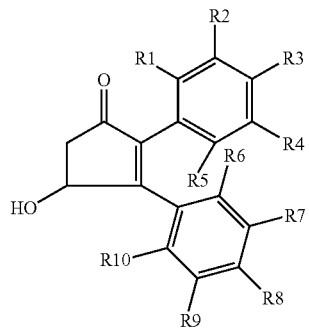

6A

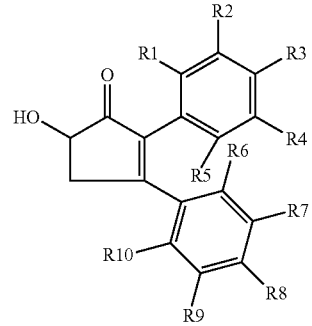

6B and other derivatives of formula (1)

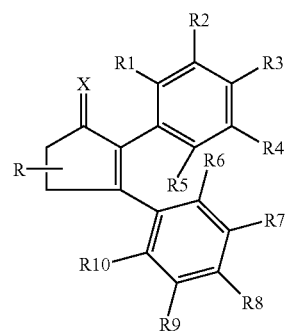

1 is shown in Schemes 1 and 2. According to one embodiment of the invention furan was treated with a strong base selected from methyllithium, n-butyllithium, s- or t-butyl lithium, lithium diisopropyl amide (LDA) and substituted benzaldehydes of the Formula 2 at −40° to 0° C. to obtain substituted furfuryl alcohol of the formula (3)

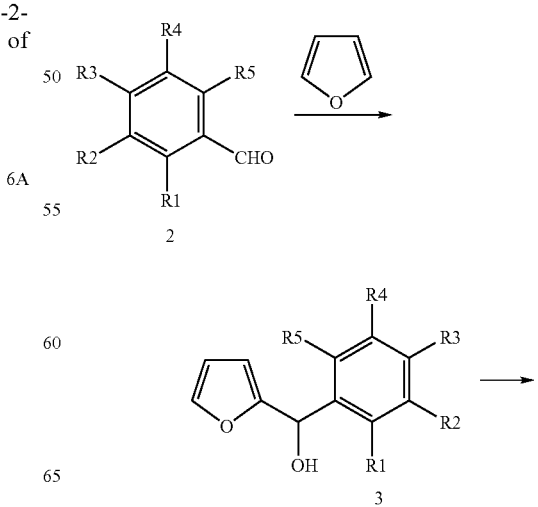

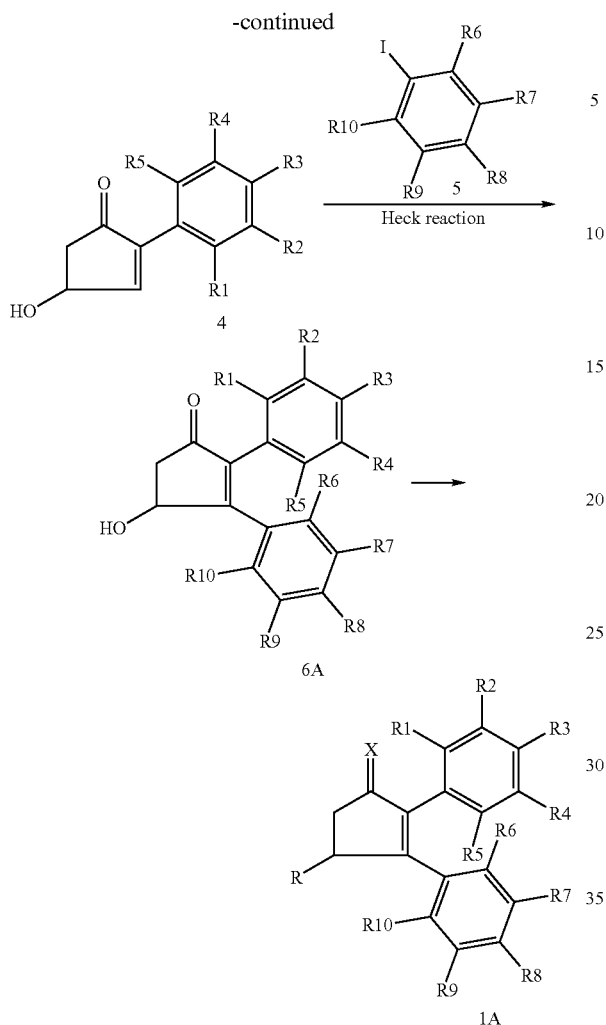

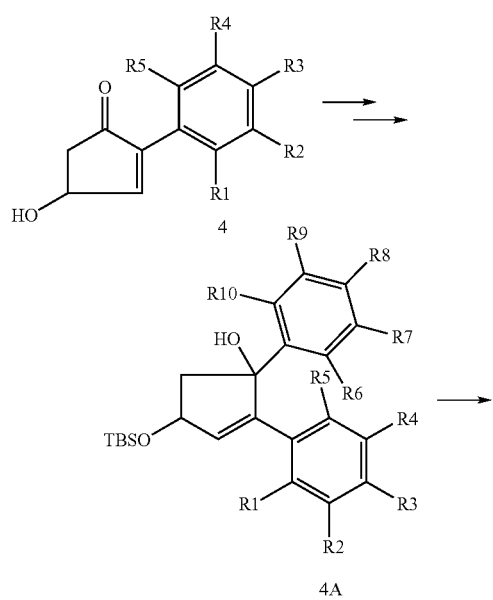

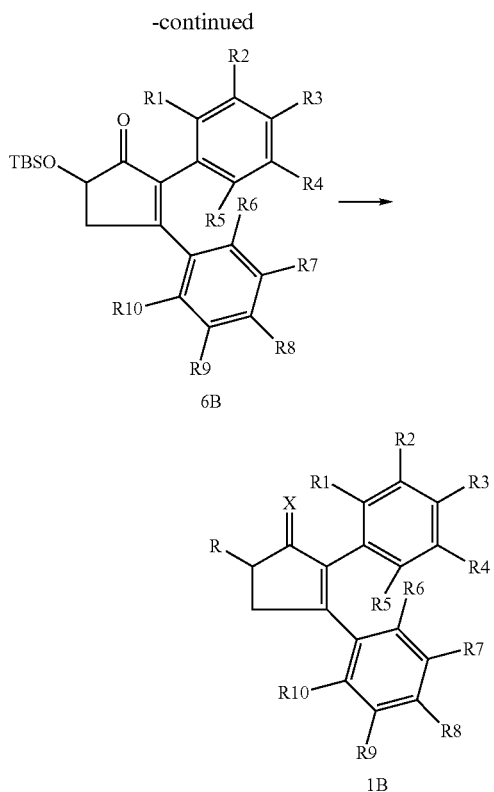

Treatment of the compound of the formula (3) with a Lewis acid preferably zinc chloride resulted in the formation of 2-aryl-4-hydroxy-cyclopent-2-en-1-one of the formula (4)

Unlike the prior art G. Piancatelli, A. Scettri, and S. Barbadoro, Tet. Lett. 39, 3555–3558 (1976); G. Piancatelli and A. Scettri, Tet. Lett. 13, 1131–1134 (1977); G. Piancatelli, A. Scettri, G. David and M. D. Auria, Tetrahedron 34, 2775–2778 (1978); A. Scettri, G. Piancatelli, M. D. Auria and G. David, Tetrahedron 35, 135–138 (1979); P. W. Collins, S. W. Kramer and G. W. Gullikson, J. Med. Chem. 30, 1952–1955 (1987); P. W. Collins, S. W. Kramer, A. F. Gasiecki, R. M. Weier, P. H. Jones, G. W. Gullikson, R. G. Bianchi, and R. F. Bauer, J. Med. Chem. 30, 193–197 (1987); M. D. Auria, Heterocycles, 52, 185–194 (2000) which disclose a two step process for preparing compounds of formula (4), in applicant's process to obtain 2-aryl-4-hydroxycyclopent-2-en-1-one of the formula (4), the double rearrangement of substituted furfuryl alcohols of the formula (3) occurs in one pot.

Compounds of the formula (4) under Heck reaction conditions using properly substituted iodobenzenes of the formula (5) provided 2,3-diaryl-4-hydroxycyclopent-2-en-1-one of the formula (6A).

Standard derivatisation techniques have been employed for converting compounds of the formula (4) and (6A) into 4-acetoxy, 4-tert.-butyldimethysilyoxy, and 4-trimethylsilyoxy derivatives (See for example Scheme 3). In order to increase the solubility of the designed molecules oximation of the cyclic ketone, oxidation of 4-hydroxy group and further dioximation was conducted by routine procedures.

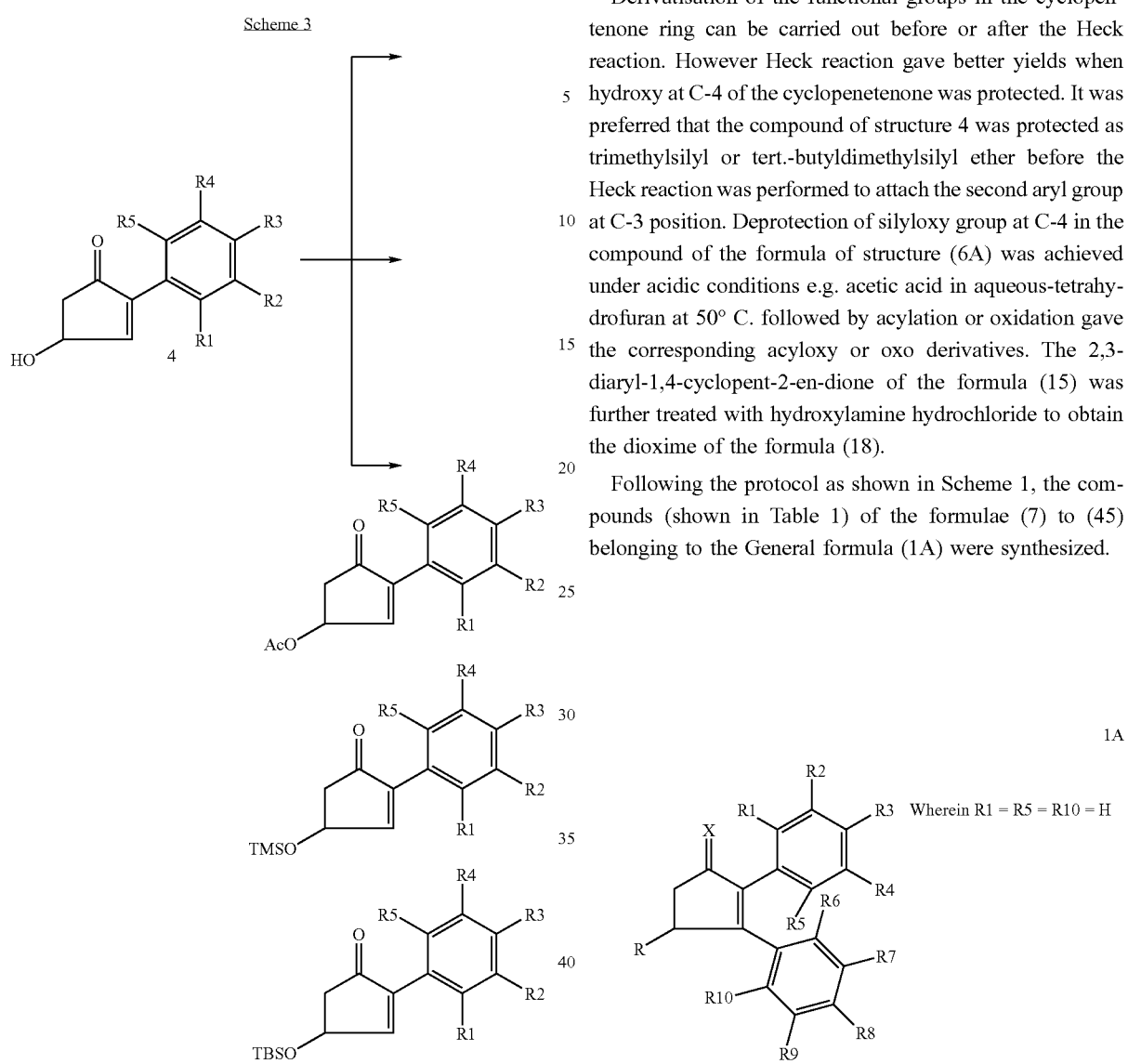

Scheme 3

Derivatisation of the functional groups in the cyclopentenone ring can be carried out before or after the Heck reaction. However Heck reaction gave better yields when hydroxy at C-4 of the cyclopenetenone was protected. It was preferred that the compound of structure 4 was protected as trimethylsilyl or tert.-butyldimethylsilyl ether before the Heck reaction was performed to attach the second aryl group at C-3 position. Deprotection of silyloxy group at C-4 in the compound of the formula of structure (6A) was achieved under acidic conditions e.g. acetic acid in aqueous-tetrahydrofuran at 50° C. followed by acylation or oxidation gave the corresponding acyloxy or oxo derivatives. The 2,3-diaryl-1,4-cyclopent-2-en-dione of the formula (15) was further treated with hydroxylamine hydrochloride to obtain the dioxime of the formula (18).

Following the protocol as shown in Scheme 1, the compounds (shown in Table 1) of the formulae (7) to (45) belonging to the General formula (1A) were synthesized.

TABLE 1

| Compound of formula No. | R | R2 | R3 | R4 | R6 | R7 | R8 | R9 | X |
|---|---|---|---|---|---|---|---|---|---|
| 7 | OH | OMe | OMe | OMe | H | H | OMe | H | O |
| 8 | OH | OMe | OMe | OMe | H | Me | OMe | Me | O |
| 9 | OH | OMe | OMe | OMe | OMe | H | H | OMe | O |
| 10 | OTBS | OMe | OMe | OMe | H | H | OMe | H | O |
| 11 | OTBS | OMe | OMe | OMe | H | H | H | H | O |
| 12 | OTBS | OMe | OMe | OMe | H | Me | OMe | Me | O |
| 13 | OTBS | OMe | OMe | OMe | OMe | H | H | OMe | O |
| 14 | OAc | OMe | OMe | OMe | H | H | OMe | H | O |
| 15 | O | OMe | OMe | OMe | H | H | OMe | H | O |
| 16 | OH | OMe | OMe | OMe | H | H | OMe | H | N—OH |
| 17 | O | OMe | OMe | OMe | H | H | OMe | H | N—OH |
| 18 | N—OH | OMe | OMe | OMe | H | H | OMe | H | N—OH |
| 19 | OTBS | OMe | OMe | OMe | H | H | OMe | H | N—OH |
| 20 | OAc | OMe | OMe | OMe | H | H | OMe | H | N—OH |
| 21 | OTBS | OMe | OMe | OMe | OMe | H | H | OMe | N—OH |

TABLE 1-continued

| Compound of formula No. | R | R2 | R3 | R4 | R6 | R7 | R8 | R9 | X |
|---|---|---|---|---|---|---|---|---|---|
| 22 | OTBS | H | H | H | H | H | H | H | O |
| 23 | OTBS | OMe | OMe | OMe | H | COOMe | OMe | H | O |
| 24 | OTBS | OMe | OMe | OMe | H | OMe | OMe | H | O |
| 25 | OTBS | H | OMe | NO₂ | H | H | OMe | H | O |
| 26 | OAc | OMe | OMe | OMe | H | Me | OMe | Me | O |
| 27 | OAc | OMe | OMe | OMe | H | Me | OMe | Me | N—OH |
| 28 | OTBS | OMe | OMe | OMe | H | OMe | OMe | H | N—OH |
| 29 | OAc | OMe | OMe | OMe | H | OMe | OMe | H | N—OH |
| 30 | OH | OMe | OMe | OMe | H | OMe | OMe | H | O |
| 31 | OH | OMe | OMe | OMe | OMe | H | OMe | OMe | N—OH |
| 32 | OAc | OMe | OMe | OMe | OMe | H | OMe | OMe | N—OH |
| 33 | OH | H | H | H | H | H | H | H | N—OH |
| 34 | OAc | H | H | H | H | H | H | H | N—OH |
| 35 | OAc | H | H | H | H | H | H | H | O |
| 36 | OH | H | H | H | H | H | H | H | O |
| 37 | OAc | OMe | OMe | OMe | OMe | H | H | OMe | O |
| 38 | OTBS | OMe | OMe | OMe | H | OMOM | OMe | H | O |
| 39 | OH | OMe | OMe | OMe | H | OH | OMe | H | O |
| 40 | OTBS | OMe | OMe | OMe | H | OMOM | OMe | H | N—OH |
| 41 | OTBS | OMe | OMe | OMe | H | OH | OMe | H | O |
| 42 | OH | OMe | OMe | OMe | H | OH | OMe | H | N—OH |
| 43 | OH | OMe | OMe | OMe | H | OMOM | OMe | H | O |
| 44 | OAc | OMe | OMe | OMe | H | OMOM | OMe | H | O |
| 45 | OH | OMe | OMe | OMe | H | OMOM | OMe | H | N—OH |

* OMOM represents methoxymethyloxy

The tert-butyldimethylsilyl derivative of Compounds of the formula (4) under Grignard reaction conditions using properly substituted iodobenzenes of the formula (5) or reaction of aryl lithium from the formula (5) afforded the corresponding 1,2-diaryl-4-(tert-butyldimethylsilyloxy)-cyclopent-2-en-1-ols having the formula (4A), which are subjected to a pyridinium dichromate catalyzed rearrangement to yield the title 2,3-diaryl-5-(tert-butyldimethylsilyloxy)-cyclopent-2-en-1-ones of the formula (6B) as shown in Scheme 2.

Following the protocol as shown in Scheme 2, the compounds (shown in 2) of the formulae (46) to (73) belonging to the of General formula (1B) were synthesized.

TABLE 2

1B

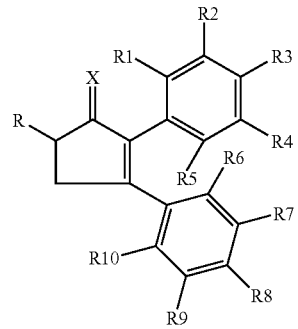

Wherein R1 = R5 = R6 = R10 = H

| Compound of formula No | R | X | R2 | R3 | R4 | R7* | R8 | R9 |
|---|---|---|---|---|---|---|---|---|
| 46 | OH | O | NO₂ | OMe | H | OMe | OMe | OMe |
| 47 | OH | N—OH | NO₂ | OMe | H | OMe | OMe | OMe |
| 48 | OH | O | OMe | OMe | OMe | H | OMe | H |
| 49 | OH | N—OH | OMe | OMe | OMe | H | OMe | H |
| 50 | OH | O | OMe | OMe | OMe | OiPr | OMe | H |
| 51 | OH | N—OH | OMe | OMe | OMe | OiPr | OMe | H |
| 52 | OTBS | O | OMe | OMe | OMe | H | OMe | H |
| 53 | OAc | O | OMe | OMe | OMe | H | OMe | H |
| 54 | OAc | N—OH | OMe | OMe | OMe | H | OMe | H |
| 55 | OTBS | O | OMe | OMe | OMe | H | SMe | H |
| 56 | OTBS | O | OMe | OMe | OMe | OiPr | OMe | H |
| 57 | OTBS | N—OH | OMe | OMe | OMe | OiPr | OMe | H |

TABLE 2-continued

1B

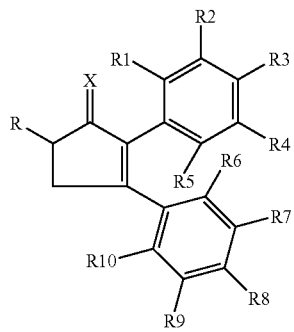

Wherein R1 = R5 = R6 = R10 = H

| Compound of formula No | R | X | R2 | R3 | R4 | R7* | R8 | R9 |
|---|---|---|---|---|---|---|---|---|
| 58 | OH | N—OH | OMe | OMe | OMe | OH | OMe | H |
| 59 | OAc | NOAc | OMe | OMe | OMe | OiPr | OMe | H |
| 60 | OH | O | $NH_2$ | OMe | H | OMe | OMe | OMe |
| 61 | OTBS | O | $NO_2$ | OMe | H | OMe | OMe | OMe |
| 62 | OH | N—OH | OMe | OMe | OMe | H | SMe | H |
| 63 | OH | N—OH | OMe | OMe | OMe | Cl | OMe | H |
| 64 | OH | O | OMe | OMe | OMe | F | OMe | H |
| 65 | OAc | O | OMe | OMe | OMe | F | OMe | H |
| 66 | OH | N—OH | OMe | OMe | OMe | F | OMe | H |
| 67 | OH | O | OMe | OMe | OMe | Cl | OMe | H |
| 68 | OAc | O | OMe | OMe | OMe | OiPr | OMe | H |
| 69 | OAc | O | OMe | OMe | OMe | Cl | OMe | H |
| 70 | OAc | N—OH | OMe | OMe | OMe | Cl | OMe | H |
| 71 | OAc | O | OMe | OMe | OMe | OH | OMe | H |
| 72 | OH | O | OMe | OMe | OMe | NHAc | OMe | H |
| 73 | OH | N—OH | OMe | OMe | OMe | NHAc | OMe | H |
| 74 | OH | O | OMe | OMe | OMe | OH | OMe | H |
| 75 | OH | O | OMe | OMe | OMe | $OCH_2CO_2Na$ | OMe | H |

*OiPr represents isopropyloxy

Representative salts of the compounds of formula 1 include but are not limited to the following: acetate, ascorbate, benzoate, citrate, oxalate, stearate, trifluoroacetate, succinate, tartarate, lactate, fumarate, gluconate, glutamate, phosphate/diphosphate, and valerate. Other salts include Ca, Li, Mg, Na, and K salts, halides, salts of amino acids such as lysine or arginine; guanidine, ammonium, substituted ammonium salts or aluminium salts. The salts may be prepared in a conventional manner.

The present invention also provides a composition comprising a compound of formula 1, a derivative or salt thereof and a pharmaceutically acceptable carrier, diluent, or solvent. The composition may optionally and preferably contain pharmaceutically acceptable diluents, excipients, additives, fillers, lubricants, solvents, binders, stabilizers, and the like. Such diluents may include: RPMI 1649, buffered saline, isotonic NaCl, Ringer's solution, water, distilled water, polyethylene glycol (neat or in water), 2% Tween in water, dimethyl-sulfoxide to 50% in water, propylene glycol (neat or in water), phosphate buffered saline, balanced salt solution, glycerol, and other conventional fluids that are suitable for intravenous administration. Pharmaceutical compositions which provide from about 0.1 to 10 gram (preferably 0.5 to 5.0 gram) of the composition per unit dose are preferred and are conventionally prepared as tablets, lozenges, capsules, powders, aqueous or oily suspension, syrups, elixirs, and aqueous solutions. The nature of the pharmaceutical composition employed will, of course, depend on the desired route of administration.

The invention provides a method of treatment for humans, mammals, or other animals suffering from cancer or other tumors. The method may suitably comprise, consist of, or consist essentially of administering a therapeutically effective dose of the pharmaceutical composition so as to kill or inhibit the multiplication of cancer or tumor cells. The invention relates more specifically to the use of the compounds of formula (I) derivatives or salts thereof for the inhibition and/or prevention of cancer of the colon, pancreas, larynx, ovary, duodenum, kidney, oral cavity, prostate, lung, endothelial cells or leukemias.

The methods of this invention comprise, consist of, or consist essentially of administering systematically to the mammal a therapeutically effective combination of cyclopentenone derivatives. An effective dose of cyclopentenone derivatives or pharmaceutically acceptable salts of the cyclopentenone derivatives ranges from 1 mg/Kg. B. Wt to 300 mg/Kg. B. Wt (preferably 10–100 mg)/Kg. B. Wt) of the mammal, with the dose dependent on the effects sought, the manner of administration, and the cancer being treated. Systemic administration refers to oral, rectal, nasal, transdermal, and parental (i.e., intramuscular, intravenous and subcutaneous). In accordance with good clinical practice, it is preferred to administer the composition at a dose that will produce anticancer effects without causing undue harmful side effects. The composition may be administered either alone or as a mixture with other therapeutic agents such as 5-fluorouracil, methotrexate, etoposide, paclitaxel, taxotere, doxorubicin, daunarubicin, vincristine, vinblastine and other such known and established anticancer drugs.

An effective amount means that amount of a drug or pharmaceutical agent that will elicit the biological or medical response of a tissue, system, animal or human that is being sought.

Further chemical transformations to obtain the desired molecules were performed using standard methods and some of them have been presented in the following examples.

To further assist in the understanding of the present invention and not by way of limitation the following examples are presented to more clearly describe the present invention.

EXAMPLE 1

Preparation of Substituted Furfuryl Alcohols of the Formula (3)

Furyl-(3,4,5-trimethoxyphenol)methanol

Magnesium (1.68 gm, 70 mmol) was taken in three neck R.B. flask equipped with condensor, 100 ml ether followed by dibromoethane (9.5 gm, 51.02 mmol) were added with stirring at 0° C. under nitrogen atmosphere. Stirring was continued until all the magnesium reacted, then the ether was removed under vacuum until a slurry was formed. (A). In another single neck R.B. flask furan (4.76 gm, 70 mmol) in tetra-hydrofuran (100 ml) was cooled with ice-salt mixture, n-butyl lithium (2M, 35 ml, 70 mmol) was added dropwise, and the mixture was stirred at 0° C. for 45 min. (B) Furyllithium thus prepared in flask (B) was added to cold mixture in (A) through cannula, stirred at 0° C. for 5 min, brought to room temperature and stirred at room temperature for 1.5 hrs; then cooled to −20° C. (dry ice and $CCl_4$). Substituted benzaldehyde (51.02 mmol) in tetra-hydrofuran (50 ml) was added and stirred at −20° C. for 4 hr (monitored by TLC). After completion of reaction the mixture was quenched with saturated ammonium chloride solution. The mixture was allowed to warm to room temperature. Solvent was removed under reduced pressure and residue extracted with ethyl acetate. The organic layer was washed with water followed by brine, dried over sodium sulfate and concentrated to dryness under reduced pressure using a rotary evaporator. The crude residue was purified by column chromatography using silica gel (petroleum ether: acetone as eluents) to collect pure compounds of the formula of structure 3 (yield, 93%).

Spectral data of furyl-(3,4,5-trimethoxyphenyl)methanol:
$^1$H NMR($CDCl_3$+$CCl_4$): δ 2.72 (bs, 1H), 3.84 (s, 9H), 5.75 (bs, 1H), 6.15(d, J=6 Hz, 1H), 6.27–6.32 (m, 1H), 6.66(d, J=2 Hz, 2H) 7.40(bs, 1H).

Mass (m/e): 264 ($M^+$, 80), 247 (60), 233 (12), 214 (15), 189 (20), 169 (70) 161 (25), 95 (100)

EXAMPLE 2

Preparation of 2-(3,4,5-trimethoxyphenyl)-4-hydroxy-cyclopent-2-enones

A solution of aryl furfuryl alcohol i.e. compound of the formula of structure 3 wherein $R_1$ and $R_5$ are H and $R_2$–$R_4$ are $OCH_3$ (25 gm, 94.69 mmol) and $ZnCl_2$ (51.26 gm, 378.7 mmol) in dioxan (30 ml) and water (206 ml) was refluxed for 24 h at which time TLC analysis indicated the complete disappearance of starting material. The mixture was brought to room temperature, acidified to pH 1 with dilute HCl and extracted with ethyl acetate. The organic layer was washed with water, followed by brine and dried over sodium sulphate. The organic layer was concentrated under reduced pressure using rotary evaporator to collect the required 2-(3,4,5-trimethoxyphenyl)-4-hydroxy-cyclopent-2-en-1-one (21.25 gm, 85%).

Spectral data:
$^1$H NMR($CDCl_3$+$CCl_4$): δ 2.52 (d, J=18 Hz, 1H), 3.00 (dd, J=18 Hz and 6 Hz, 1H), 3.86 (s, 3H), 3.89 (s, 6H), 5.00–5.10 (m, 1H), 6.98 (s, 2H), 7.58 (d, 1H). Mass (m/e): 264 ($M^+$, 100), 249 (57), 233 (10), 221 (22), 205 (32), 189 (15), 177 (20), 161 (40).

EXAMPLE 3

Preparation of Tert-butyldimethylsilyl Derivatives

A solution of 2-aryl-4-hydroxy-cyclopent-2-en-1-one of formula (4) (8.7 mmol) in dry dichloromethane (30 ml) was stirred at 0° C. under inert atmosphere (maintained by using nitrogen or argon gas filled in balloon), a solution of tert-butyl dimethylsilyl chloride (1.5 gm, 9.95 mmol) and dimethylamino pyridine (0.194 gm, 1.5 g mmol) in dichloromethane (10 ml) was added drop wise and stirred at the same temperature for 15 min. Then triethylamine (1.77 ml, 12.7 mmol) was added and mixture was warmed to room temperature and stirred further for 3 h (monitored by TLC). The reaction mixture was filtered through whatman filter paper, dichloromethane was removed under reduced pressure and extracted with chloroform. The organic layer was washed with water, followed by brine, dried over sodium sulphate and concentrated to dryness under reduced pressure using rotary evaporator. The crude residue was purified by column chromatography using silica gel (petroleum ether: acetone as eluent) to give the title derivatives.

Spectral data of 2-(3,4,5-trimethoxyphenyl)-4-tert.-butyldimethylsilyoxy-cyclopent-2-en-1-one:
$^1$H NMR($CDCl_3$+$CCl_4$): δ 0.16 (s, 3H), 0.17 (s, 3H), 0.94 (s, 9H), 2.47 (d, J=18 Hz, 1H), 2.92 (dd, J=18 Hz and 6 Hz, 1H), 3.85 (s, 3H), 3.90 (s, 6H), 495–5.05 (m, 1H), 6.96 (s, 2H), 7.45 (d, 1H).

Mass (m/e): 378 ($M^+$, 100), 363 (10), 321 (15), 290 (40), 219 (70).

EXAMPLE 4

Preparation of 4-acetoxy-2-(3,4,5-trimethoxyphenyl)-cyclopent-2-en-1-one

A solution of 2-(3,4,5-trimethoxyphenyl)-4-hydroxy-cyclopent-2-en-1-one (3 gm, 11.36 mmol) in dichloromethane (30 ml) was cooled to 0° C. using ice-salt bath. To the cold solution dry pyridine (1.70 gm, 1.73 ml; 26.0 mmol) was added and stirred at 0° C. for 10 min. To the stirred solution, acetic anhydride (1.63 gm, 1.50 ml, 16.0 mmol) was added dropwise while maintaining the temperature below 0° C. The reaction mixture was stirred at room temperature for 15 h (monitored by TLC) then quenched by adding cold, dilute hydrochloric acid. The organic layer was washed three times with water, 10% sodium bicarbonate solution and finally brine. The organic layer was dried over sodium sulfate and concentrated to dryness under reduced pressure using a rotary evaporator. The crude residue was purified by column chromatography using silica gel (petroleum ether: acetone as eluent) to collect the pure 4-acetoxy-2-(3,4,5-trimethoxy-phenyl)-cyclopent-2-en-1-one (2.56 gm, 73.47%).

Spectral data:

$^1$H NMR(CDCl$_3$+CCl$_4$): δ 2.08 (s, 3H), 2.54 (d, J=18 Hz, 1H), 3.00 (dd, J=18 Hz and 6 Hz, 1H), 3.82 (s, 3H), 3.84 (s, 6H), 5.80–5.90 (m, 1H), 6.96 (s, 2H), 7.59 (d, J=4 Hz, 1H)

Mass (m/e): 306 (M$^+$, 100), 264 (14), 247 (34), 231 (8), 219 (51).

EXAMPLE 5

Heck Reaction of Aryl Iodides with Cyclopentenone

A mixture of of p-iodo anisole (3.71 gm, 15.87 mmol), 2-(3,4,5-trimethoxyphenyl)-4-hydroxy-cyclopent-2-enone (7.93 mmol),), palladium acetate (0.230 gm, 1.026 mmol), triphenyl phosphine, (0.400 gm, 1.52 mmol), potassium carbonate (2.20 gm, 15.86 mmol), and catalytic amount of tetrabutylammonium bromide (0.030 gm) in degassed acetonitrile was refluxed for 36 h. Then the reaction mixture was cooled to room temperature, and acetonitrile was removed under reduced pressure using a rotary evaporator. The residue was acidified with dilute HCl and then extracted with chloroform. The organic layer was washed with water followed by brine, dried over sodium sulfate and concentrated to dryness under reduced pressure, using a rotary evaporator. The crude residue was purified by column chromatography using silica gel (petroleum ether: acetone as eluent) to collect pure products of the formula of structure (7).

Spectral data of compound of the formula of structure (7)

$^1$H NMR(CDCl$_3$+CCl$_4$): δ 2.65 (d, J=18 Hz, 1H), 3.11 (dd, J=18 Hz and 8 Hz, 1H), 3.72 (s, 6H), 3.83 (s, 3H), 3.86 (s, 3H), 5.45–5.50 (m, 1H), 6.46 (s, 2H), 6.87 (d, J=10 Hz, 2H), 7.41 (d, J=10 Hz, 2H).

Mass (m/e): 370 (M$^+$, 100), 355 (19), 262 (32), 231 (20), 219 (18), 177 (30), 163 (27), 135 (25).

EXAMPLE 6

Preparation of Compound of Formula of Structure (10)

A mixture of p-iodo anisole (3.71 gm, 15.87 mmol), 2-(3,4,5-trimethoxyphenyl)-4-ter-butyldimethylsilyoxy-cyclopent-2-enone (7.93 mmol),), palladium acetate (0.230 gm, 1.026 mmol), triphenyl phosphine, (0.400 gm, 1.52 mmol), potassium carbonate (2.20 gm, 15.86 mmol), and catalytic amount of tetrabutylammonium bromide (0.030 gm) in degassed acetonitrile was refluxed for 36 h. Then the reaction mixture was cooled to room temperature, and acetonitrile was removed under reduced pressure using a rotary evaporator. The residue was acidified with dilute HCl and then extracted with chloroform. The organic layer was washed with water followed by brine, dried over sodium sulfate and concentrated to dryness under reduced pressure, using a rotary evaporator. The crude residue was purified by column chromatography using silica gel (petroleum ether: acetone as eluent) to collect pure products of the formula of structure (10).

Spectral data of compound of the formula of structure (10):

$^1$H NMR(CDCl$_3$+CCl$_4$): δ 0.05 (s, 3H), 0.09 (s, 3H), 0.80 (s, 9H), 2.57 (d, J=16 Hz, 1H), 3.02 (dd, J=16 Hz and 6 Hz, 1H), 3.69 (s, 6H), 3.82 (s, 3H), 3.84 (s, 3H), 5.30–5.40 (m, 1H), 6.44 (s, 2H), 6.82 (d, J=6 Hz, 2H), 7.27 (d, J=6 Hz, 2).

Mass (m/e): 484(M$^+$, 5), 427 (30), 369 (32), 353 (100), 325 (61), 294 (47).

EXAMPLE 7

Preparation of Compound of Formula of Structure (11)

A mixture of iodobenzene (15.87 mmol), 2-(3,4,5-trimethoxyphenyl)-4-ter-butyldimethylsilyoxy-cyclopent-2-enone (7.93 mmol), palladium acetate (0.230 gm, 1.026 mmol), triphenyl phosphine, (0.400 gm, 1.52 mmol), potassium carbonate (2.20 gm, 15.86 mmol), and catalytic amount of tetrabutylammonium bromide (0.030 gm) in degassed acetonitrile was refluxed for 36 h. Then the reaction mixture was cooled to room temperature, and acetonitrile was removed under reduced pressure using a rotary evaporator. The residue was acidified with dilute HCl and then extracted with chloroform. The organic layer was washed with water followed by brine, dried over sodium sulfate and concentrated to dryness under reduced pressure, using a rotary evaporator. The crude residue was purified by column chromatography using silica gel (petroleum ether: acetone as eluent) to collect pure products of the formula of structure (11).

Spectral data of compound of the formula structure (11):

$^1$H NMR(CDCl$_3$+CCl$_4$): δ −0.05 (s, 3H), 0.05 (s, 3H), 0.77 (s, 9H), 2.61 (d, J=18 Hz, 1H) 3.05 (dd, J=18 Hz and 6 Hz, 1H), 3.63 (s, 6H), 3.82 (s, 3H), 5.27–5.33 (m, 1H), 6.47 (s, 2H), 7.32 (bs, 5H).

Mass (m/e): 454 (M$^+$, 28), 379 (100), 323 (28), 291 (27), 247 (92), 219 (66), 75(83).

EXAMPLE 8

Preparation of Compound of Formula of Structure (12)

A mixture of 3,5-dimethyl-4-methoxy-1-iodobenzene (15.87 mmol), 2-(3,4,5-trimethoxyphenyl)-4-ter-butyldimethylsilyoxy-cyclopent-2-enone (7.93 mmol),), palladium acetate (0.230 gm, 1.026 mmol), triphenyl phosphine, (0.400 gm, 1.52 mmol), potassium carbonate (2.20 gm, 15.86 mmol), and catalytic amount of tetrabutylammonium bromide (0.030 gm) in degassed acetonitrile was refluxed for 36 h. Then the reaction mixture was cooled to room temperature, and acetonitrile was removed under reduced pressure using a rotary evaporator. The residue was acidified with dilute HCl and then extracted with chloroform. The organic layer was washed with water followed by brine, dried over sodium sulfate and concentrated to dryness under reduced pressure, using a rotary evaporator. The crude residue was purified by column chromatography using silica gel (petroleum ether: acetone as eluent) to collect pure products of the formula of structure 12.

Spectral data of compound of the formula of structure 12:

$^1$H NMR(CDCl$_3$+CCl$_4$): δ −0.01 (s, 3H), 0.07(s, 3H), 0.78(s, 9H), 2.20(s, 6H), 2.56(d, J=18 Hz, 1H) 3.01(dd, J=18 Hz and 6 Hz, 1H), 3.68(s, 6H), 3.70(s, 3H), 3.83(s, 3H), 5.20–5.30(m, 1H), 6.51(s, 2H), 6.97 (s, 2H).

Mass (m/e): 512 (M$^+$, 18), 456 (38), 425 (16), 381 (51), 353 (15), 322 (13) 129(100).

EXAMPLE 9

Preparation of Compound of Formula of Structure 13

A mixture of 2,5-dimethoxy-1-iodobenzene (15.87 mmol), 2-(3,4,5-trimethoxyphenyl)-4-ter-butyldimethylsilyoxy-cyclopent-2-enone (7.93 mmol), palladium acetate (0.230 gm, 1.026 mmol), triphenyl phosphine, (0.400 gm, 1.52 mmol), potassium carbonate (2.20 gm, 15.86 mmol), and catalytic amount of tetrabutylammonium bromide (0.030 gm) in degassed acetonitrile was refluxed for 36 h. Then the reaction mixture was cooled to room temperature, and acetonitrile was removed under reduced pressure using a rotary evaporator. The residue was acidified with dilute HCl and then extracted with chloroform. The organic layer was washed with water followed by brine, dried over sodium sulfate and concentrated to dryness under reduced pressure, using a rotary evaporator. The crude residue was purified by column chromatography using silica gel (petroleum ether: acetone as eluent) to collect pure products of the formula of structure 13.

Spectral data of compound of the formula of structure 13:

$^1$H NMR(CDCl$_3$+CCl$_4$): δ −0.19 (s, 3H),−0.04 (s, 3H), 0.74 (s, 9H), 2.55 (d, J=16 Hz, 1H), 3.02 (dd, J=16 Hz and 6 Hz, 1H), 3.63 (s, 6H), 3.65 (s, 3H), 3.69 (s, 3H), 3.78 (s, 3H), 5.25–5.38 (m, 1H), 6.45–6.72 (m, 3H), 6.75–6.96 (m, 2H).

Mass (m/e): 514 (M$^+$, 71), 458 (87), 443 (30), 384 (40), 154 (70) 75 (100).

Example 10 describes a general method for deprotection of tert-butyldimethylsilyloxy group used in preparation of various compounds described in this specification. The compounds of the formula 8 and 9 are specific compounds obtained using this method from their corresponding TBS derivatives, i.e. compound 8 is obtained from compound 12 and compound 9 is obtained from compound 13.

EXAMPLE 10

Deprotection of Tert-butyldimethylsilyloxy Derivatives

A solution of protected 4-tert-butyldimethylsilyloxy-2,3-diarylcyclopent-2-enone (0.72 mmol) in acetic acid; tetrahydrofuran and water (3:1:1) was heated at 50° C. for 20 h (monitored by TLC). The reaction mixture was cooled to 0° C. and neutralized by sodium bicarbonate and extracted with chloroform. The organic layer was washed with water followed by brine and dried over sodium sulfate and filtered. The filtrate was concentrated to dryness under reduced pressure using a rotary evaporator. The crude residue was purified by column chromatography using silica gel (petroleum ether: acetone as eluent) to collect the 4-hydroxy-2,3-diarylcyclopentenone of the general formula of structure 6.

Spectral data of compounds of the formula of structure 8:

$^1$H NMR(CDCl$_3$+CCl$_4$): δ 2.21 (s, 6H), 2.63 (d, J=18 Hz, 1H), 3.07 (dd, J=18 Hz and 6 Hz, 1H), 3.69 (s, 6H), 3.71 (s, 3H), 3.84 (s, 3H), 5.35–5.45 (m, 1H), 6.47 (s, 2H), 7.06 (s, 2H).

Mass (m/e): 398 (M$^+$, 100), 367 (5), 262 (32), 247 (51), 231 (12), 177 (15), 149 (13).

Spectral data of compounds of the formula of structure 9:

$^1$H NMR(CDCl$_3$+CCl$_4$): δ 2.63 (dd, J=18 Hz and 2 Hz, 1H), 3.06 (dd, J=18 Hz and 6 Hz, 1H), 3.59 (s, 3H), 3.64 (s, 6H), 3.71 (s, 3H), 3.80 (s, 3H), 5.35–5.50 (m, 1H), 6.45–6.75 (m, 3H), 6.84–7.00 (m, 2H).

Mass (m/e): 400 (M$^+$, 19), 369 (3), 111 (82), 83 (52), 71 (67).

EXAMPLE 11

Preparation of Compound of the Formula of Structure 14

A solution of 2-(3,4,5-trimethoxyphenyl)-3-(4-methoxyphenyl)-4-hydroxy-cyclopent-2-en-1-one (0.235 gm, 0.63 mmol) in dichloromethane (20 ml) was cooled to 0° C. using ice-salt bath. To the cold solution dry pyridine (0.10 gm, 1.46.0 mmol) was added and stirred at 0° C. for 10 min. To the stirred solution, acetic anhydride (0.10 gm, 0.95 mmol) was added drop wise while maintaining the temperature below 0° C. The reaction mixture was stirred at room temperature for 15 h (monitored by TLC) then quenched by adding cold, dilute hydrochloric acid. The organic layer was washed three times with water, 10% sodium bicarbonate solution and finally brine. The organic layer was dried over sodium sulfate and concentrated to dryness under reduced pressure using a rotary evaporator. The crude residue was purified by column chromatography using silica gel (petroleum ether: acetone as eluent) to collect the pure 2-(3,4,5-trimethoxyphenyl)-3-(4-methoxyphenyl)-4-acetoxy-cyclopent-2-en-1-one (0.21 gm, 80.45%).

Spectral data:

$^1$H NMR(CDCl$_3$+CCl$_4$): δ 2.01 (s, 3H), 2.52 (d, J=18 Hz, 1H), 3.15 (dd, J=18 Hz and 6 Hz, 1H), 3.71 (s, 6H), 3.81 (s, 3H), 3.85 (s, 3H), 6.40 (m, 1H), 6.44 (s, 2H), 6.81 (d, J=8 Hz, 2H), 7.26 (d, J=8 Hz, 2H).

Mass (m/e): 412 (M$^+$, 100), 397 (8), 352 (13), 337 (17).

EXAMPLE 12

Preparation of Diketone of the Structure 15

A solution of pyridinium chlorochromate (0.300 gm) in dichloromethane (20 ml) was cooled to 0° C., stirred for 5 minutes, then a solution of 2,3-diaryl-4-hydroxy cyclopentenone of the formula 7, (0.200 gm, 0.54 mmol) in dichloromethane (5 ml) was added and stirred for 2 hours at room temperature (monitored by TLC). The reaction mixture was filtered through celite. The filtrate was washed with water followed by brine and dried over sodium sulfate, and concentrated to dryness under reduced pressure using a rotary evaporator. The crude residue was purified by column chromatography using silica gel (petroleum ether: acetone as eluents) to collect pure cyclopentenedione of the structure 15 (0.060 gm, 30.16%).

Spectral data:

$^1$H NMR(CDCl$_3$+CCl$_4$): δ 3.17 (s, 2H), 3.69 (s, 6H), 3.83 (s, 3H), 3.88 (s, 3H), 6.63 (s, 2H), 6.88 (d, J=6 Hz, 2H), 7.38 (d, J=6 Hz, 2H).

Mass (m/e): 368 (M$^+$, 100), 353 (30), 283 (23), 169 (20), 111 (46) 69 (70).

EXAMPLE 13

Preparation of Oxime of the Structure 16

A mixture of ketone of the formula 7 (0.100 gm, 0.20 mmol), hydroxyl amine hydrochloride (0.02 gm, 0.30 mmol) and sodium acetate (0.025 gm, 0.30 mmol) in ethanol (5 ml) was refluxed on water bath for 3 h. The reaction was monitored by TLC and after completion of reaction the solvent was removed under reduced pressure using a rotary evaporator. The residue was extracted with chloroform. The organic layer was washed with water followed by brine and dried over sodium sulfate and concentrated to dryness under reduced pressure using a rotary evaporator. The crude residue was purified by column chromatography using silica gel (petroleum ether: acetone as eluent) to collect pure oxime of the structure 16 (0.086 gm, 83.50%).

Spectral data:
$^1$H NMR(CDCl$_3$+CCl$_4$): δ 2.80 (d, J=18 Hz, 1H), 3.36 (dd, J=18 Hz and 8 Hz, 1H), 3.73 (s, 6H), 3.79 (s, 3H), 3.87 (s, 3H), 5.30–5.40 (m, 1H), 6.47 (s, 2H), 6.80 (d, J=8 Hz, 2H), 7.26 (d, J=8 Hz, 2H).

Mass (m/e): 385 (M$^+$, 100), 368 (40), 336 (12).

EXAMPLE 14

Preparation of Oxime of Structure 17 from Compound of Structure 16

A solution of pyridinium chlorochromate (0.080 gm) in dichloromethane (10 ml) was cooled to 0° C., stirred for 5 minutes, then a solution of 2,3-diaryl-4-hydroxy cyclopentenone of the formula 16, (0.075 gm, 0.19 mmol) in dichloromethane (5 ml) was added and stirred for 2 hours at room temperature (monitored by TLC). The reaction mixture was filtered through celite and the filtrate was washed with water followed by brine and dried over sodium sulfate, and concentrated to dryness under reduced pressure using rotary evaporator. The crude residue was purified by a column chromatography using silica gel (petroleum ether: acetone as eluents) to collect pure cyclopentenedione of the structure 17 (0.026 gm, 35%).

Spectral data compound of the structure 17:
$^1$H NMR(CDCl$_3$+CCl$_4$): δ 3.41 (s, 2H), 3.69 (s, 6H), 3.80 (s, 3H), 3.89 (s, 3H), 6.58 (s, 2H), 6.83 (d, J=9 Hz, 2H), 7.24 (d, J=9 Hz, 2H), 8.60 (bs, 1H).

Mass (m/e): 384 (M$^+$, 100), 367 (37), 336 (34), 307 (12).

EXAMPLE 15

Preparation of Oxime of the Structure 19

A mixture of ketone of the formula 10 (0.100 gm, 0.20 mmol), hydroxyl amine hydrochloride (0.02 gm, 0.30 mmol) and sodium acetate (0.025 gm, 0.30 mmol) in ethanol (5 ml) was refluxed on water bath for 3 h. The reaction was monitored by TLC and after completion of the reaction the solvent was removed under reduced pressure using rotary evaporator. The residue was extracted with chloroform, the organic layer was washed with water followed by brine and dried over sodium sulfate and concentrated to dryness under reduced pressure using a rotary evaporator. The crude residue was purified by column chromatography using silica gel (petroleum ether: acetone as eluent) to collect pure oxime of the structure 19 (0.086 gm, 83.50%).

Spectral data:
$^1$H NMR(CDCl$_3$+CCl$_4$): δ −0.01 (s, 3H), 0.08 (s, 3H), 0.82 (s, 9H), 2.70 (d, J=18 Hz, 1H), 3.32 (dd, J=18 Hz and 6 Hz, 1H), 3.69 (s, 6H), 3.78 (s, 3H), 3.84 (s, 3H), 5.24–5.30 (m, 1H), 6.46 (s, 2H), 6.76 (d, J=9 Hz, 2H), 7.14 (d, J=9 Hz, 2H), 7.85 (bs, 1H).

Mass (m/e): 499 (M$^+$, 68), 442 (67), 368 (100), 320 (12), 74 (60).

EXAMPLE 16

Preparation of Dioxime of the Structure 18

A mixture of diketone of the formula 15 (0.060 gm, 0.16 mmol), hydroxylamine hydrochloride (0.026 gm, 0.40 mmol) and sodium acetate (0.033 gm, 0.40 mmol) in ethanol (5 ml) was refluxed on a water bath for 3 hrs. (monitored by TLC). Then the solvent was removed under reduced pressure using a rotary evaporator and the residue obtained was extracted with chloroform. The organic layer was washed with water followed by brine and dried over sodium sulfate, concentrated to dryness under reduced pressure using a rotary evaporator. The crude residue was purified by column chromatography using silica gel (petroleum ether: acetone as eluent) to collect pure dioxime of the structure 18 (0.033 gm, 51.6%).

Spectral data:
$^1$H NMR(CDCl$_3$+CCl$_4$): δ 3.42 (s, 2H), 3.47 (s, 6H), 3.61 (s, 3H), 3.64 (s, 3H), 6.36 (s, 2H), 6.60 (d, J=6 Hz, 2H), 7.06 (d, J=6 Hz, 2H).

EXAMPLE 17

Preparation of Compound of the Structure 20

A mixture of ketone of the formula 14 (0.100 gm, 0.24 mmol), hydroxylamine hydrochloride (0.023 gm, 0.36 mmol) and sodium acetate (0.03 gm, 0.36 mmol) in ethanol (5 ml) was refluxed on a water bath for 3 h. The reaction was monitored by TLC and after completion of reaction the solvent was removed under reduced pressure using a rotary evaporator. The residue was extracted with chloroform, the organic layer was washed with water followed by brine and dried over sodium sulfate and concentrated to dryness under reduced pressure using a rotary evaporator. The crude residue was purified by column chromatography using silica gel (petroleum ether: acetone as eluent) to collect pure oxime of the structure 20 (0.088 gm, 85.40%).

Spectral data of compound of structure 20:
$^1$H NMR(CDCl$_3$+CCl$_4$): δ 2.02 (s, 3H), 2.72 (d, J=18 Hz, 1H), 3.40 (dd, J=18 Hz and 6 Hz, 1H), 3.72 (s, 6H), 3.78 (s, 3H), 3.87 (s, 3H), 6.25–6.35 (m, 1H), 6.46 (s, 2H), 6.75 (d, J=10 Hz, 2H), 7.12 (d, J=10 Hz, 2H).

Mass (m/e): 427 (M$^+$, 100), 412 (7), 369 (47), 351 (25), 320 (31), 305 (7).

The compound of the formula of structure 21 was prepared from a compound of the formula of stru7cture 13 by using the same procedure as above.

Spectral data of compound of the formula of structure (21):
$^1$H NMR(CDCl$_3$+CCl$_4$): δ −0.21 (s, 3H), −0.06 (s, 3H), 0.76 (s, 9H), 2.69 (d, J=18 Hz, 1H), 3.36 (dd, J=18 Hz and 6 Hz, 1H), 3.64 (s, 3H), 3.66 (s, 6H), 3.70 (s, 3H), 3.80 (s, 3H), 5.20–5.30 (m, 1H), 6.50–6.57 (m, 3H), 6.76 (bs, 2H), 7.99 (bs, 1H).

Mass (m/e): 529 (M$^+$, 63), 512 (71), 472 (100), 398 (68), 75 (60).

EXAMPLE 18

Preparation of 5-tert-Butyldimethylsilyloxy-3-(4-methoxy-3-i-propoxyphenyl)-2-(3,4,5-trimethoxyphenyl)-cyclopent-2-en-1-one of the formula (56)

4-Iodo-2-i-propoxyanisole (1.94 g, 7.90 mmol) in dry tetrahydrofuran (10 ml) was stirred under nitrogen at −78°

C. and n-butyl lithium (3.45 ml of 2.3 M solution, 7.90 mmol) was added dropwise. The reaction mixture was stirred at −78° C. for 1.5 h. 4-tert-Butyldimethylsilyloxy-2-(3,4,5-trimethoxyphenyl)-cyclopent-2-en-1-one (2.00 g, 5.29 mmol) in dry tetrahydrofuran (10 ml) was added and the reaction mixture was stirred at −78° C. for 12 h. It was then quenched with saturated ammonium chloride solution (30 ml), tetrahydrofuran was removed under reduced pressure, extracted with dichloromethane (3×50 ml), washed with water (2×20 ml) followed by brine (1×20 ml), dried (sodium sulfate), concentrated and purified by column chromatography over silica gel (eluent-8% acetone in pet ether) to afford the compound of the formula (4A) wherein $R_1=R_5=R_6=R_7=R_{10}=H$, $R_2=R_3=R_4=R_8=OMe$, $R_9=Oi\text{-}Pr$ (1.28 g, 45%) as yellowish semisolid.

The above alcohol of the formula (4A) wherein $R_1=R_5=R_6=R_7=R_{10}=H$, $R_2=R_3=R_4=R_8=OMe$, $R_9=Oi\text{-}Pr$ (0.50 g, 0.92 mmol) in dry dichloromethane (15 ml) was stirred with pyridinium dichromate (0.69 g, 1.83 mmol) under nitrogen at room temperature for 4 h. It was then filtered through celite (3.00 g), washed with dichloromethane (50 ml), concentrated and purified by column chromatography over silica gel (eluent-5% acetone in pet ether) to afford the title compound of the formula (56) (0.42 g, 79%).

Spectral data of compound of the formula of structure (56)

$^1$H NMR (CDCl$_3$+CCl$_4$): δ 0.21 (s, 6H), 0.96 (s, 9H), 1.13 (d, J=6 Hz, 3H), 1.16 (d, J=6 Hz, 3H), 2.92(dd, J=18 Hz, and 6 Hz, 1H), 3.33 (dd, J=18 Hz and 6 Hz, 1H) 3.74 (s, 6H), 3.81 (s, 6H), 3.85 (s, 3H), 4.01–4.06 (m, 1H), 4.45–4.50 (m, 1H), 6.41 (s, 2H), 6.80 (d, J=8 Hz, 1H), 6.83 (d, J=2 Hz, 1H), 7.08 (dd, J=8 Hz and 2 Hz, 1H).

$^{13}$C NMR(CDCl$_3$+CCl$_4$): δ −5.19, −4.42, 18.30, 21.61, 21.75, 25.76 (3C), 39.07, 55.61, 55.79 (2C), 60.46, 71.05, 106.33 (2C), 111.04, 115.71, 121.62, 127.21, 128.39, 135.78, 137.65, 146.51, 152.17, 153.42 (2C), 162.39, 204.77, 205.00

EXAMPLE 19

Preparation of O-tert-Butyldimethylsilyloxy-3-(4-methoxyphenyl)-2-(3,4,5-trimethoxyphenyl)-cyclopent-2-en-1-one of formula (52)

Magnesium turnings (0.19 g, 7.93 mmol) were taken in a 100 ml round bottom flask under nitrogen atmosphere. Dry tetrahydrofuran (25 ml) was added followed by dropwise addition of p-bromoanisole (1.48 g, 7.90 mmol). The reaction mixture was stirred at room temperature for 2 h by which time all the magnesium reacted to form 4-methoxyphenyl magnesium bromide. 4-tert-Butyldimethylsilyloxy-2-(3,4,5-trimethoxyphenyl)-cyclopent-2-en-1-one (2.00 g, 5.29 mmol) in dry tetrahydrofuran (15 ml) was added and stirred at room temperature for 2 h. It was then quenched with dil hydrochloric acid (25 ml), tetrahydrofuran was removed under reduced pressure, reaction mixture was extracted with ethyl acetate (3×25 ml), washed with water (2×25 ml), dried over sodium sulfate, concentrated and purified by column chromatography over silica gel (eluent-7% acetone in pet ether) to yield the alcohol of the formula (4A) wherein $R_1=R_5=R_6=R_7=R_9=R_{10}=H$, $R_2=R_3=R_4=R_8=OMe$ (1.28 g, 52%).

The above alcohol of the formula (4A) wherein $R_1=R_5=R_6=R_7=R_9=R_{10}=H$, $R_2=R_3=R_4=R_8=OMe$ (1.15 g, 2.36 mmol) was dissolved in dry dichloromethane (30 ml) and stirred under nitrogen with pyridinium dichromate (1.73 g, 7.38 mmol) under nitrogen at room temperature for 12 h. Workup as in example 1 and purification by column chromatography over silica gel (eluent-3% acetone in pet ether afforded the title compound of the formula (52) (0.52 g, 45%).

Spectral data of compound of the formula of structure (52)

$^1$H NMR (CDCl$_3$+CCl$_4$): δ 0.23 (s, 6H), 0.97 (s, 9H), 2.94 (dd, J=16 Hz and 4 Hz, 1H), 3.30 (dd, J=16 Hz and 8 Hz, 1H), 3.74 (s, 6H), 3.81 (s, 3H), 3.85 (s, 3H), 4.45–4.52 (m, 1H), 6.44 (s, 2H), 6.80 (d, J=8 Hz, 2H), 7.35 (d, J=8 Hz, 2H)

EXAMPLE 20

Preparation of 5-tert-Butyldimethylsilyloxy-3-(4-thiomethylphenyl)-2-(3,4,5-trimethoxyphenyl)-cyclopent-2-en-1-one of formula (55)

4-Bromothioanisole (1.07 g, 5.28 mmol) and magnesium metal (0.12 g, 5.28 mmol) were placed in a 100 ml two-necked round bottom flask under argon atmosphere. Dry tetrahydrofuran (10 ml) was added and the mixture was stirred at room temperature for 2 h. It was then cooled to 0° C., 4-tert-butyldimethysilyloxy-2-(3,4,5-trimethoxyphenyl)-cyclopent-2-en-1-one (1.00 g, 2.64 mmol) in dry tetrahydrofuran (10 ml) was added dropwise, stirred at 0° C. for ½ h and then at room temperature for 2 h. The reaction was then quenched with saturated ammonium chloride solution (50 ml) and tetrahydrofuran was removed under reduced pressure. The residual reaction mixture was extracted with ethyl acetate (3×50 ml), washed with water (2×20 ml) followed by brine (10 ml), dried (sodium sulfate) and concentrated. Purification by column chromatography over silica gel (eluent-7% acetone in pet ether) afforded the compound of formula (4A) wherein $R_1=R_5=R_6=R_7=R_9=R_{10}=H$, $R_2=R_3=R_4=OMe$, $R_8=SMe$ (0.95 g, 72%).

The above compound of formula (4A) wherein $R_1=R_5=R_6=R_7=R_9=R_{10}=H$, $R_2=R_3=R_4=OMe$, $R_8=SMe$ (0.65 g, 1.29 mmol) in dry dichloromethane (10 ml) was cooled to 0° C., pyridinium dichromate (0.96 g, 2.5 mmol) was added, the mixture was stirred at the same temperature for 1 h and then stirred at room temperature for 10 h. It was then filtered through celite (2.00 g) and washed with dichloromethane (20 ml).The combined dichloromethane layer was washed with water (2×10 ml) followed by brine (5 ml), dried (sodium sulfate), concentrated and purified by column chromatography over silica gel (eluent-2–5% acetone in pet ether) to afford the compound of formula (55) (0.30 g, 46%).

Spectral data of compound of the formula of structure (55)

$^1$H NMR (CDCl$_3$+CCl$_4$): δ 0.23 (s, 6H), 0.98 (s, 9H), 2.48 (s, 3H), 2.96 (dd, J=16 Hz and 4 Hz, 1H), 3.30 (dd, J=16 Hz and 6 Hz, 1H), 3.74 (s, 6H), 3.86 (s, 3H), 4.45–4.60 (m, 1H), 6.44 (s, 2H), 7.31 (d, J=8 Hz, 2H).

$^{13}$C NMR(CDCl$_3$): δ −5.23, −4.53, 14.70, 18.22, 25.69 (3C), 39.25, 55.83 (2C), 60.57, 72.84, 106.44 (2C), 125.12 (2C), 127.01, 128.57(2C), 131.11, 136.40, 137.80, 142.06, 153.16 (2C), 162.13, 204.92

Mass (m/z): 500 (M$^+$)

EXAMPLE 21

Preparation of 5-Hydroxy-3-(3-chloro-4-methoxyphenyl)-2-(3,4,5-trimethoxyphenyl)-cyclopent-2-en-1-one of formula (67)

A mixture of magnesium turnings (0.31 g, 13.1 mmol), 2-chloro-4-bromoanisole (3.00 g, 13.5 mmol), 4-tert-butyldimethysilyloxy-2-(3,4,5-trimethoxy-phenyl)-cyclopent-2-en-1-one (2.58 g, 6.84 mmol) and dry tetrahydrofuran (35 ml) under nitrogen was stirred at room temperature for 4 h. Reaction was then quenched with dil hydrochloric acid (30 ml), tetrahydrofuran was removed under reduced pressure and the residual reaction mixture was extracted with ethyl acetate (3×35 ml), washed with water (2×20 ml) and dried over sodium sulfate. Concentration and purification by column chromatography over silica gel (eluent-6% acetone in pet ether) afforded the alcohol of the formula (4A) wherein $R_1=R_5=R_6=R_7=R_{10}=H$, $R_2=R_3=R_4=R_8=OMe$, $R_9=Cl$ (1.32 g, 37%).

A solution of the above alcohol of the formula (4A) wherein $R_1=R_5=R_6=R_7=R_{10}=H$, $R_2=R_3=R_4=R_8=OMe$, $R_9=Cl$ wherein (0.95 g, 1.83 mmol) in dry dichloromethane (15 ml) was cooled to 0° C., pyridinium dichromate (1.92 g, 8.17 mmol) was added and the mixture was stirred at room temperature for 3 h. Filtration through celite (3.00 g), washing with dichloromethane (30 ml) and concentration afforded the crude product which was purified by silica gel column chromatography (eluent-3% acetone in pet ether) to yield the title compound of the formula (1B) wherein R=OTBS, $R_1=R_5=R_6=R_7=R_{10}=H$, $R_2=R_3=R_4=R_8=OMe$, $R_9=Cl$ (0.32 g, 34%), which on deprotection of TBDMS group using the procedure described in example 10 furnished the compound of formula (67).

Spectral data of compound of the formula of structure (67)

$^1$H NMR (CDCl$_3$+CCl$_4$): δ 2.96 (dd, J=18 Hz and 2 Hz, 1H), 3.33 (dd, J=18 Hz and 6 Hz, 1H), 3.75 (s, 6H), 3.86 (s, 3H), 3.91 (s, 3H), 4.45–4.54 (m, 1H), 6.42 (s, 2H), 6.81 (d, J=8 Hz, 1H), 7.21–7.29 (m, 1H), 7.48 (bs, 1H).

$^{13}$C-NMR (CDCl$_3$+CCl$_4$): δ 37.79, 55.87 (2C), 60.58, 71.57, 106.23 (2c), 111.31, 122.41, 126.82, 127.59, 128.58 (2C), 130.05, 135.90, 138.07, 153.36 (2C), 156.48, 162, 51, 206.95

EXAMPLE 22

Preparation of 5-Hydroxy-3-(3-fluoro-4-methoxyphenyl)-2-(3,4,5-trimethoxyphenyl)-cyclopent-2-en-1-one of formula (64)

4-Bromo-2-fluoroanisole (1.08 g, 5.29 mmol) and magnesium metal (0.13 g, 5.29 mmol) were placed in a 100 ml two-necked round bottom flask under argon atmosphere. Dry tetrahydrofuran (10 ml) was added and the mixture was stirred at room temperature for 2 h. It was then cooled to 0° C., 4-tert-butyldimethysilyloxy-2-(3,4,5-trimethoxyphenyl)-cyclopent-2-en-1-one (1.00 g, 2.64 mmol) in dry tetrahydrofuran (10 ml) was added dropwise, stirred at 0° C. for 1 h and then at room temperature for 2 h. The reaction was then quenched with saturated ammonium chloride solution (50 ml) and tetrahydrofuran was removed under reduced pressure. The residual reaction mixture was extracted with ethyl acetate (3×50 ml), washed with water (2×20 ml) followed by brine (10 ml), dried (sodium sulfate) and concentrated. Purification by column chromatography over silica gel (eluent-5–8% acetone in pet ether) afforded the compound of formula (4A) wherein $R_1=R_5=R_6=R_7=R_{10}=H$, $R_2=R_3=R_4=R_8=OMe$, $R_9=F$ (1.20 g, 90%).

The above compound of formula (4A) wherein $R_1=R_5=R_6=R_7=R_{10}=H$, $R_2=R_3=R_4=R_8=OMe$, $R_9=F$ (0.50 g, 1.00 mmol) in dry dichloromethane (10 ml) was cooled to 0° C., pyridinium dichromate (0.47 g, 2.00 mmol) was added, the mixture was stirred at the same temperature for 1 h and then stirred at room temperature for 8 h. It was then filtered through celite (2.00 g) and washed with dichloromethane (20 ml). The combined dichloromethane layer was washed with water (2×10 ml) followed by brine (5 ml), dried (sodium sulfate), concentrated and purified by column chromatography over silica gel (eluent-2–5% acetone in pet ether) to afford the compound of formula (1B) wherein R=OTBS, $R_1=R_5=R_6=R_7=R_{10}=H$, $R_2=R_3=R_4=R_8=OMe$, $R_9=F$ (0.24 g, 48%), which on deprotection of TBDMS group using the procedure described in example 10 furnished the compound of formula (64)

Spectral data of compound of the formula of structure (64)

$^1$H-NMR (CDCl$_3$+CCl$_4$): δ 2.93 (dd, J=16 Hz and 4 Hz, 1H), 3.30 (dd, J=16 Hz and 6 Hz, 1H), 3.70 (s, 6H), 3.82 (s, 3H), 3.85 (s, 3H), 4.45–4.60 (m, 1H), 6.40 (s, 2H), 6.78–6.91 (m, 1H), 7.00–7.20 (m, 2H).

$^{13}$C-NMR (CDCl$_3$): δ 37.86, 55.84 (2C), 60.58, 71.50, 106.16 (2C), 112.56, 115.72, 116.12, 125.35, 127.00 (2C), 136.01, 137.92, 149.28, 149.50, 153.32 (2C), 162.80, 207.17.

Mass (m/z): 388 (M$^+$).

EXAMPLE 23

Preparation of 5-Hydroxy-2-(4-methoxy-3-nitrophenyl)-3-(3,4,5-trimethoxyphenyl)-cyclopent-2-en-1-one of formula (46)

3,4,5-Trimethoxyiodobenzene (0.20 g, 0.68 mmol) in dry tetrahydrofuran (7 ml) was stirred under nitrogen at −78° C. and n-butyl lithium (0.3 ml of 2.3 M solution, 0.68 mmol) was added dropwise. The reaction mixture was stirred at the same temperature for 1.5 h and then 4-tert-butyldimethysilyloxy-2-(3,4,5-trimethoxyphenyl)-cyclopent-2-en-1-one (0.25 g, 0.68 mmol) in dry tetrahydrofuran (5 ml) was added dropwise. The reaction mixture was stirred at −78° C. for ½ h and at RT for 1 h. It was then quenched with saturated ammonium chloride solution (10 ml), tetrahydrofuran was removed under reduced pressure, product was extracted with ethyl acetate (2×15 ml) washed with water (1×10 ml), dried (sodium sulfate), concentrated and purified by column chromatography over silica gel (eluent-10% acetone in pet ether) to afford the compound of the formula (4A) wherein $R_1=R_4=R_5=R_6=R_{10}=H$, $R_3=R_7=R_8=R_9=OMe$, $R_2=NO_2$ (0.14 g, 40%).

The above alcohol of formula (4A) wherein $R_1=R_4=R_5=R_6=R_{10}=H$, $R_3=R_7=R_8=R_9=OMe$, $R_2=NO_2$ (0.10 g, 0.19 mmol) in dry dichloromethane (10 ml) was refluxed with pyridinium dichromate (0.14 g, 0.37 mmol) for 18 h under nitrogen atmosphere. It was then filtered through celite (2.00 g) and washed with dichloromethane (30 ml). The combined dichloromethane layer was washed with water (2×10 ml) followed by brine (5 ml), dried (sodium sulfate), concentrated and purified by column chromatography over silica gel (eluent-10% acetone in pet ether) to afford the compound of formula (1B) wherein R=OTBS, $R_1=R_4=R_5=R_6=R_{10}=H$, $R_3=R_7=R_8=R_9=OMe$, $R_2=NO_2$ (0.06 g, 52%), which on deprotection of TBDMS group using the procedure described in example 10 furnished the compound of formula (46)

Spectral data of compound of the formula of structure (46)

$^1$H NMR (CDCl$_3$+CCl$_4$): δ 3.02 (bd, J=16 Hz, 1H), 3.27 (dd, J=16 Hz and 6 Hz, 1H) 3.68 (s, 6H), 3.88 (s, 3H), 3.97 (s, 3H), 4.53 (bs, 1H, D$_2$O exchangeable), 5.28–5.30 (m, 1H), 6.59 (s, 2H), 7.07 (d, J=8 Hz, 1H), 7.45 (bd, J=8 Hz, 1H), 7.79 (bs, 1H)

EXAMPLE 24

Preparation of Compound of the Formula (58) from the Compound of the Formula (51)

A mixture of compound of the formula (51) (0.300 gm, 0.67 mmol), aluminium chloride (0.180 gm, 1.35 mmol) and benzene (10 ml) was stirred at 50° C. under argon atmosphere. It was then cooled and quenched with cold dilute hydrochloric acid (10 ml) and extracted with ethyl acetate (2×2 0 ml). The organic layer was washed with water (2×15 ml) followed by brine (10 ml), dried over sodium sulfate and concentrated under reduced pressure. Purification by column chromatography over silica gel (eluent 8%, 10% acetone in petroleum ether) afforded pure compound of the formula (58) (0.180 gm, 66%).

Spectral data of compound of the formula of structure (58)

$^1$H NMR (CDCl$_3$+CCl$_4$): δ 2.94 (bd, J=18 Hz, 1H), 3.32 (dd, J=18 Hz and 8 Hz, 1H), 3.76 (s, 6H), 3.88 (s, 6H), 5.29–5.40 (m, 1H), 6.44 (s, 2H), 6.65–6.75 (m, 2H), 6.84 (bs, 1H)

Mass (m/z): 401 (M$^+$).

EXAMPLE 25

Preparation of Compound of the Formula (42) from the Compound of the Formula (40)

A mixture of compound of the formula (40) (0.100 gm) and tetrahydrofuran-acetic acid-water (3:1:1, 20 ml) was heated at 50° C. for 20 hr. It was then neutralized by aq. ammonia and extracted with ethyl acetate, dried over sodium sulfate, concentrated and purified by column chromatography to yield pure compound of the formula (42) (0.070 gm, 77%).

Spectral data of compound of the formula of structure (42)

$^1$H NMR (CDCl$_3$+CCl$_4$): δ 2.68 (bd, J=18 Hz, 1H), 3.00 (dd, J=18 Hz and 6 Hz, 1H), 3.70 (s, 6H), 3.84 (s, 6H), 5.18–5.35 (m, 1H), 6.43 (s, 2H), 6.62–6.80 (m, 2H), 6.88 (bs, 1H).

EXAMPLE 26

In Vitro Cytotoxicity of the Cyclopentenone Derivatives

A number of the cyclopentenone derivatives were tested for cytotoxicity against 9 human tumor cell lines. Briefly, a three day MTT cytotoxicity assay was performed, which is based on the principle of uptake of MTT (3-(4,5-dimethylthiazol-2-yl)-2,5-diphenyl tetrazolium bromide), a tetrazolium salt, by the metabolically active cells where it is metabolized by active mitochondria into a blue colored formazan product that is read spectrophotometrically. MTT was dissolved in phosphate buffered saline with a pH of 7.4 to obtain an MTT concentration of 5 mg/ml; the resulting mixture was filtered through a 0.22 micron filter to sterilize and remove a small amount of insoluble residue. For each type of tumor cell, 10000 to 15000 cells were seeded in a 96-well culture plate and incubated with the individual cyclopentenone derivatives in a CO$_2$ incubator for a total of 72 hours. Control cells not treated with the cyclopentenone derivatives were similarly incubated. The assay was terminated by adding 100 ug (20 ul) of MTT to each well, then incubating for additional one hour, and finally adding 50 ul of 10% SDS-0.01N HCl to each well to lyse the cells and dissolve formazan. After incubating for one hour, the plate was read spectrophotometrically at 540 nm and the percentage of cytotoxicity calculated using the following formula:

Cytotoxicity percentage=100×[1−(X/R$_1$)], where X=(absorbance of treated sample at 540 nm)−(absorbance of blank at 540 nm)

R$_1$=absorbance of control sample at 540 nm.

The ED$_{50}$ Values of the cytotoxicity defined as the concentration at which 50% of the cells are killed in vitro was calculated for each cell line treated with each of the cyclopentenone derivatives.

The cell lines are PTC (all colon), MOLT-4 (leukemia), SW620 (ovary), DU145 (prostate), KB (oral squamous cell), L132 (lung), MIAPaCa2 (Pancreas), Hep2, (larynx), PA-1 (ovary), HuTu80 (duodenum), ECV 304 (endothelial), and 293 (kidney).

The ED$_{50}$ values of in vitro cytotoxicity of the cyclopentenone derivatives of this invention are shown in the Table 3.

TABLE 3

ED$_{50}$ VALUES (UG/ML) OF CYTOTOXICITY OF CYCLOPENTENONE DERIVATIVES IN CANCER CELL LINES IN VITRO.

| S No | Compound of formula No | ED50 (ug/ml) | | | | | | | | | | |
|---|---|---|---|---|---|---|---|---|---|---|---|---|
| | | PTC | MOLT4 | SW620 | DU145 | KB | L132 | MiaPaca | Hep2 | PA1 | HuTu80 | ECV 304 | 293 |
| 1 | 20 | ND | <1 | 1.5 ± 0.1 | 2.0 ± 0.1 | 5 ± 1.1 | 20 ± 3.5 | 1.0 ± 0.1 | 3 ± 1.1 | 20 ± 3.5 | 20 ± 4.5 | 4 ± 1.5 | 32 ± 4.5 |
| 2 | 22 | ND | ND | 1.0 ± 0.1 | 15 ± 3.5 | ND | 40 ± 5.0 | 1.0 ± 0.1 | 4.0 ± 1.0 | ND | ND | 4.0 ± 1.0 | 5.0 ± 1.5 |

TABLE 3-continued

ED$_{50}$ VALUES (UG/ML) OF CYTOTOXICITY OF CYCLOPENTENONE DERIVATIVES IN CANCER CELL LINES IN VITRO.

| S No | Compound of formula No | PTC | MOLT4 | SW620 | DU145 | KB | L132 | MiaPaca | Hep2 | PA1 | HuTu80 | ECV 304 | 293 |
|---|---|---|---|---|---|---|---|---|---|---|---|---|---|
| 3 | 39 | 78 ± 4.0 | 62.5 ± 5.0 | <1 | 8 ± 1.5 | <1 | <1 | >100 | <1 | <1 | 1.5 ± 0.1 | >100 | >100 |
| 4 | 40 | 14.2 ± 3.5 | 11 ± 2.1 | <1 | 30 ± 3.5 | 27 ± 4.0 | 28 ± 3.5 | 6 ± 1.5 | 13.7 ± 2.5 | 8 ± 1.6 | 14 ± 3.1 | 16.5 ± 4.0 | 18 ± 3.5 |
| 5 | 42 | >100 | 72.2 ± 5.0 | 9 ± 3.1 | 23 ± 4.5 | 10 ± 2.5 | 8 ± 1.4 | >100 | <1 | 3.7 ± 1.5 | 23.5 ± 4.0 | >100 | >100 |
| 6 | 48 | 6.0 ± 1.5 | <1.0 | <1.0 | >100 | 8 ± 2.1 | 9.0 ± 3.3 | 79 ± 9.5 | <1.0 | <1.0 | ND | >100 | ND |
| 7 | 49 | <1.0 | <1.0 | <1.0 | >100 | <1.0 | <1.0 | 24 ± 3.5 | <1.0 | <1.0 | ND | >100 | ND |
| 8 | 52 | 16 ± 3.6 | 3.0 ± 1.5 | 5.0 ± 1.0 | 28 ± 4.0 | 7.0 ± 3.0 | 9.0 ± 2.5 | <1.0 | 16 ± 3.0 | 7.0±3.5 | ND | 16 ± 4.0 | ND |
| 9 | 53 | 6.0 ± 1.5 | <1.0 | <1.0 | >100 | 72 ± 5.5 | >100 | <1.0 | 18 ± 3.5 | <1.0 | ND | 18 ± 3.0 | ND |
| 10 | 54 | 1.5 ± 2.5 | <1.0 | <1.0 | >100 | 69 ± 9.5 | ND | <1.0 | >100 | <1.0 | ND | >100 | ND |
| 11 | 55 | 14 ± 3.5 | <1.0 | <1.0 | >100 | 10 ± 1.5 | <1.0 | <1.0 | >100 | <1.0 | ND | >100 | ND |
| 12 | 56 | >100 | 22.5 ± 4.0 | 9 ± 1.5 | 6.3 ± 2.1 | 7.5 ± 3.5 | 7± | >100 | 7.1 ± 1.5 | 7.1 ± 1.5 | 6 ± 0.5 | >100 | >100 |
| 13 | 57 | >100 | >100 | 8 ± 1.5 | >100 | <1 | 54± | >100 | 84 ± 2.5 | >100 | <1 | >100 | >100 |
| 14 | 60 | >100 | >100 | <1 | 41 ± 5.0 | <1 | 54± | >100 | 16 ± 1.5 | 20± | <1 | >100 | >100 |
| 15 | 63 | 15 ± 3.0 | ND | <1 | 16 ± 4.5 | 9.8 ± 3.1 | <1 | 33 ± 4.0 | <1 | ND | 26 ± 4.0 | 18.5 ± 3.5 | 50 ± 4.5 |
| 16 | 64 | 20 ± 2.5 | ND | <1 | 27 ± 3.5 | 4.5 ± 1.5 | <1 | 64 ± 3.5 | <1 | ND | <1 | 19.5 ± 4.5 | >100 |
| 17 | 65 | 80 ± 5.7 | ND | <1 | 16 ± 4.0 | 33 ± 2.5 | <1 | 39.5 ± 4.0 | <1 | ND | 28 ± 5.0 | 41 ± 4.5 | 59 ± 4.0 |
| 18 | 66 | 27 ± 3.5 | ND | <1 | 10 ± 5.1 | <1 | <1 | 94 ± 10.0 | <1 | ND | 9 ± 3.1 | 43 ± 4.5 | >100 |
| 19 | 67 | 30 ± 4.0 | ND | <1 | 40 ± 8.5 | 2.5 ± 0.1 | <1 | >100 | <1 | ND | 29 ± 2.5 | 20 ± 3.5 | >100 |
| 20 | 70 | ND | ND | <1 | 17 ± 5.0 | 50 ± 5.0 | <1 | 10 ± 1.5 | ND | ND | 65 ± 8.0 | ND | 32 ± 4.0 |
| 21 | 71 | ND | ND | <1 | >100 | <1 | 30 ± 5.1 | >100 | 12 | 2 | 50 | >100 | >100 |
| 22 | 72 | ND | ND | 6 ± 1.5 | >100 | 10 ± 1.5 | 88 ± 10.0 | >100 | 9 ± 1.5 | 74 ± 5.5 | 78 ± 5.5 | >100 | 77 ± 5.0 |
| 23 | 73 | ND | ND | 4 ± 1.5 | >100 | 8 ± 4.5 | 68 ± 7.5 | 96± | 8 ± 2.0 | 45 ± 4.5 | 85 ± 5.0 | >100 | >100 |

NA: Not active (ED$_{50}$ > 100 ug/ml)

EXAMPLE 27

The cyclopentenone derivatives were checked for their effects on tubulin polymerization in in vitro. Briefly, the tubulin assembly reaction was performed at 37° C. in buffer containing 80 mM PIPES, 1 mM EGTA, 1.0 mM GTP and 1 mM MgCl$_2$ (pH 6.9) at a tubulin concentration of 1 mg/ml in the presence or absence of the cyclopentenone derivatives. The final concentration of the cyclopentenone derivatives in the reaction mixture varied from 1–5 uM. The derivatives were dissolved in 0.1% DMSO. The control experiments were carried out with 0.1% DMSO. The tubulin polymerization was followed by measurement of the absorbance of the solution at 340 nm every 30 seconds. The IC50 values for the inhibition of Tubulin Polymerization by the cyclopentenone derivative are shown in Table 4. As shown below the cyclopentenones derivatives inhibited the Tubulin polymerization with IC50 values ranging from 1.4–2.9uM in vitro. Thus the cyclopentenone derivatives mediated their observed anticancer activities by tubulin depolymerization.

TABLE 4

IC50 values for inhibition of Tubulin Polymerization by Cyclopentenone derivatives

| S. No | Compound of formula No | IC50 values (uM) for inhibition of Tubulin Polymerization |
|---|---|---|
| 1 | 48 | 2.1 ± 0.1 |
| 2 | 49 | 2.3 ± 0.5 |
| 3 | 39 | 1.4 ± 0.6 |
| 4 | 66 | 2.0 ± 0.6 |
| 5 | 74 | 1.8 ± 0.5 |

EXAMPLE 28

Human squamous cell carcinoma (KB) were plated in a 25 cm$^2$ flask. When cultures achieved confluence, the cyclopentenone derivative of structure 20 was added to cells. The final concentration of derivative of the structure 20 in the flask was 5 ug/ml. The untreated wells served as controls. The cells were incubated with the drug for 2 different time points of 6 and 16 hours at 37° C. The cells were collected by centrifugation at 2000 r.p.m. for 10 minutes. The supernatant was gently removed and discarded while Lysis Buffer was added to the cell pellet (25 ul of lysis buffer per $1\times10^4$ cell). The cell lysate was incubated on ice for 10 minutes and centrifuged at 10,000-×g for 1 minute. The supernatant was transferred to a new tube and kept on ice. 50 ul of the cell lysate was added in a 96 well plate. To this was added 2× Reaction Buffer. Prior to using reaction buffer 10 ul of fresh DTT stock per 1 ml of 2× Reaction Buffer was added. To each well 5 ul of Caspase-3 colorimetric substrate (DEVD-pNA) was added. The plate was incubated for 1–2 hours at 37° C. and read at 405 nm.

The level of caspase enzymatic activity in the cell lysate is directly proportional to the absorbance at 405 nm. Table 5 shows the level of induction of Caspase 3 in KB cells treated with one of the cyclopentenone derivatives.

TABLE 5

Caspase-3 Induction caused by Cyclopentenone Derivatives in Oral Cancer Cells (KB)

| Molecule | Percent Induction of Caspase-3 | |
|---|---|---|
|  | 6 hours | 16 hours |
| 20 | 13.6 ± 2.4 | 20.7 ± 3.1 |
| 39 | 12.8 ± 0.2 | 17.0 ± 1.5 |
| 48 | 18.4 ± 1.1 | 22.7 ± 1.5 |
| 49 | 26.7 ± 2.8 | 31.9 ± 3.2 |
| 66 | 17.0 ± 1.0 | 22.1 ± 0.6 |
| 74 | 21.8 ± 2.8 | 28.4 ± 2.1 |

EXAMPLE 29

Human endothelial cells (ECV304) were plated at the density of $8-10\times10^5$ cells per 2 ml in a six well plate. After an overnight incubation of cells at 37° C., cyclopentenone derivatives at a concentration of 5 ug/ml was added to the wells. The untreated wells served as controls. The plates were incubated for 4 hours at 37° C. The medium was collected from all the wells (control and treated) and spun down at 2000 r.p.m to remove the cellular material. The supernatant was collected and used for ELISA (quantikine human VEGF, R&D Systems). The assay employs the quantitative sandwich enzyme immuonoassay technique. A monoclonal antibody specific for VEGF has been pre-coated onto a microplate. Standards and samples were pipetted into the wells and VEGF present was bound by the immobilized antibody. After washing away the unbound substances, an enzyme-linked polyclonal antibody specific for VEGF was added to the wells. Following a wash to remove any unbound antibody-enzyme reagent, a substrate solution was added to the wells and color developed in proportion to the amount of VEGF bound in the initial step. The optical density of each well was determined within 30 minutes using a microplate reader set to 450 nm and reference wavelength at 540 nm. The VEGF levels were inhibited by the addition of cyclopentenone derivatives in vitro. The present reduction in the inhibition of VEGF by the cyclopentenone derivatives is shown in Table 6.

TABLE 6

Percent reduction in VEGF levels in endothelial cells (ECV304) treated with cyclopentenone derivatives in vitro

| Compound | Percent Reduction in VEGF |
|---|---|
| 13 | 11.3 ± 2.4 |
| 20 | 2.0 ± 0.1 |
| 21 | 16.2 ± 3.4 |
| 48 | 23.7 ± 2.2 |
| 49 | 28.6 ± 1.9 |
| 39 | 21.9 ± 1.5 |
| 66 | 12.9 ± 2.9 |
| 74 | 16.9 ± 0.5 |

A PubMed search of the National Library of Medicine was carried out to determine the relevance of the cell lines used by us for determining the anticancer activity of the peptides. While HT29 (human colon) showed 2021 "hits" when searched with reference to cancer, other human cancer cell lines used by us also showed large number of hits (6848 for K562, 2532 for MOLT-4, 542 for DU145, 1063 for MCF-7, 542 for DU145 and 182 for PA-1). This clearly shows the extensive use of these cell lines in cancer research. Further, it is a common and standard practice and norm for testing molecules for anticancer activity in vitro on human tumor cell lines. (Br J Cancer. 2001 May 18; 84(10): 1289–90 Flasks, Fibers and Flanks—Preclinical tumor models for predicting clinical antitumor activity). The authors report that in vitro activity against 6 or more lung or breast cancer cell lines does predict xenograft activity against these tumor types. In articles "Semin Oncol 1992 December; 19;(6):622–38 (The National Cancer Institute: cancer drug discovery and development program) and "Jpn J Antibiot 1977 Dec. 30; Suppl:35–40 (Antitumor screening procedures of the National Cancer Institute)" extensive use of human tumor cell lines for identification of potential cytotoxic drugs is described."

EXAMPLE 30

In Vivo Anti-tumor Activity of Compound of Formula No. 49 on Primary Tumor (Colon) Xenografted Mice PTC tumor xenografts were grown in Balb/c athymic mice by subcutaneous inoculation of a single cell suspension of PTC cells ($15\times10^6$ cells/100 μL). The tumor bearing animals were divided into 2 groups of three animals each including one group comprising untreated control animals. Treatment with compound of formula no. 49 was initiated when the average tumor volumes, as measured using a vernier caliper, were between 500 mm³. Compound of formula no. 49 was administered intravenously to the assigned group of tumor bearing animals at a dose of 0.5 mg/100 μL once a day and the treatment was continued for a period of 14 days.

The antitumor activity of the compound was monitored by measuring tumor volumes every fourth day using the formula W*W*L*0.4 (W=smaller diameter, L=larger diameter). The percentage inhibition of tumor growth was calculated using the formula (1-tumor volume-treated/tumor volume-control)*100. FIG. 1 shows the tumor kinetics till day 23 in the treated and untreated animals. Compound of formula no. 49 showed significant antitumor activity on PTC xenografts. The percentage inhibition of tumor growth caused compound of formula no. 49 as compared to controls on day 23 was 45.8%.

The invention claimed is:

1. A compound of the Formula 1,

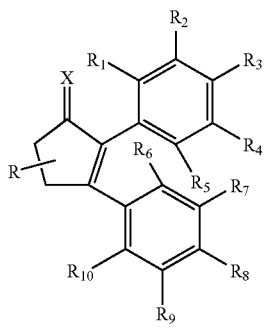

or a salt thereof, wherein X is oxygen, hydroxyimino, alkoxyimino, aryloxyimino or arylimino; R is hydroxy, oxo, amino, alkylamino, hydroxyimino, alkoxyimino, aryloxyimino, alkylcarbonyloxy, aroyloxy, methoxymethyloxy, 2-methoxyethoxymethyloxy, tert-butyldimethylsilyloxy, trimethylsilyloxy, carboxyl acid, carboxylate salt, or carboxylic acid ester; $R_1$, $R_2$ and $R_4$ to $R_{10}$ are the same or different and represent hydrogen, hydroxy, alkyl, alkoxy, methoxymethyloxy, 2-methoxyethoxymethyloxy, tert-butyldimethylsilyloxy, trimethylsilyloxy, chloro, fluoro, bromo, mercapto, alkylthio, nitro, amino, monoalkylamino, dialkylamino, azido, carboxyl, carbalkoxy, alkylcarbonyloxy, carboxymethyloxy, $NHCOCH_3$, $NHCOCF_3$, NH-alkyl, NH-dialkyl, CN, guanidine, $NHCOOR_{11}$, $CH_2C=NR_{12}NR_{13}$; $NHNH_2$, $NHCONH_2$, $NHNHCONH_2$, $NHNHC(=S)NH_2$ and their salts; $OPO_3H_2$, $OPO_3Na_2$, $OPO_3K_2$, $SO_2NH_2$, CONH-alkyl, CHO, CH=NOH, or —($CH_2$—$CH_2$—N)— fused at $R_8$, $R_9$ positions respectively, or methylenedioxy group fused in lieu of either $R_8$, $R_9$ or $R_9$, $R_{10}$ position, respectively, and in the latter $R_8$ is alkoxy; $R_{11}$, $R_{12}$, and $R_{13}$, are selected from $C_1$–$C_4$ alkyl groups, and $R_3$ is alkoxy.

2. A compound according to claim 1, wherein the cyclopentenone is cyclopent-2-en-1-one.

3. A compound according to claim 1, wherein the cyclopentenone derivative is a cyclopent-2-en-1-one derivative with R at C-4 position represented by formula (1A)

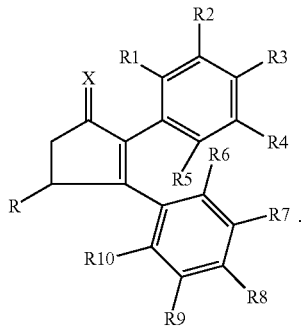

4. A compound according to claim 1, wherein the cyclopentenone is a cyclopent-2-en-1-one derivative with R at C-5 position represented by formula (1B)

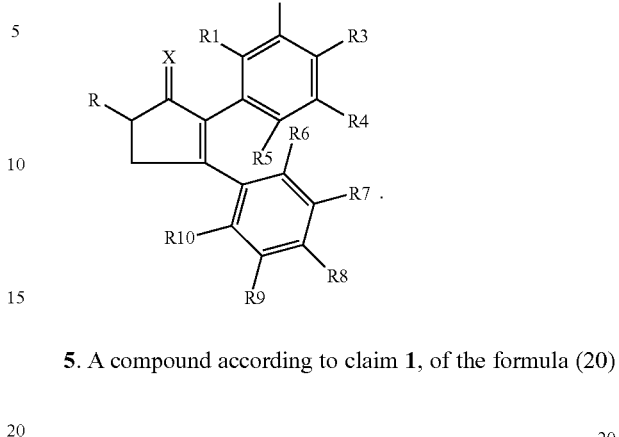

5. A compound according to claim 1, of the formula (20)

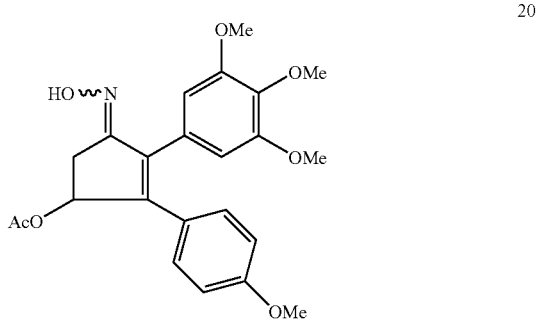

and is 2-(3,4,5-trimethoxyphenyl)-3-(4-methoxyphenyl)-4-acetoxy-cyclopent-2-en-1-one oxime.

6. A compound according to claim 1, having formula (22)

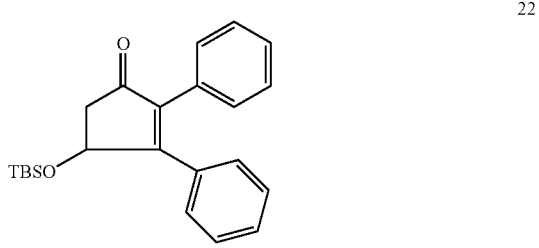

and is 2,3-diphenyl-4-(tert. butyldimethysilyloxy)cyclopent-2-en-1-one.

7. A compound according to claim 1, having formula (39)

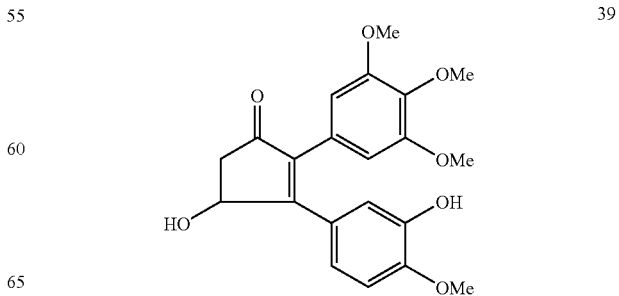

and is 2-(3,4,5-trimethoxyphenyl)-3-(3-hydroxy-4-methoxyphenyl)-4-hydroxy-cyclopent-2-en-1-one.

8. A compound according to claim 1, having formula (40)

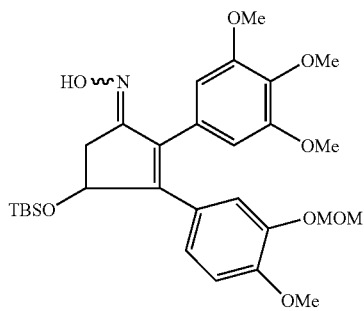

and is 2-(3,4,5-trimethoxyphenyl)-3-(3-methoxymethyloxy-4-methoxyphenyl)-4-(tert. butyldimethysilyloxy)-cyclopent-2-en-1-one oxime.

9. A compound according to claim 1, having formula (42)

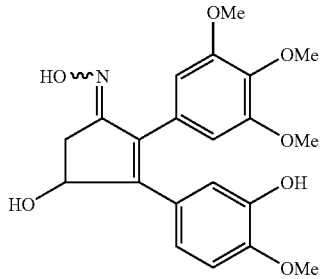

and is 2-(3,4,5-trimethoxyphenyl)-3-(3-hydroxy-4-methoxyphenyl)-4-hydroxy-cyclopent-2-en-1-one oxime.

10. A compound according to claim 1, having formula (48)

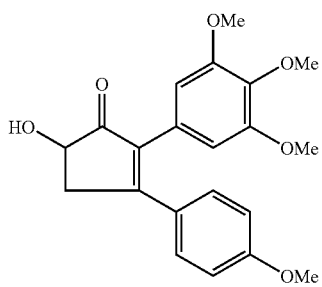

and is 2-(3,4,5-trimethoxyphenyl)-3-(4-methoxyphenyl)-5-hydroxy-cyclopent-2-en-1-one.

11. A compound according to claim 1, having formula (49)

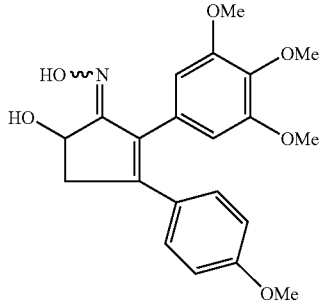

and is 2-(3,4,5-trimethoxyphenyl)-3-(4-methoxyphenyl)-5-hydroxy-cyclopent-2-en-1-one oxime.

12. A compound according to claim 1, having formula (52)

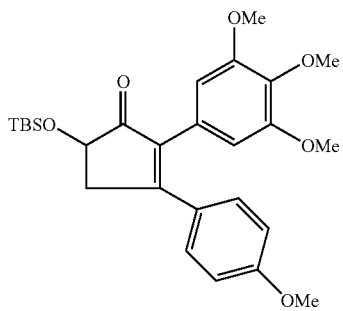

and is 2-(3,4,5-trimethoxyphenyl)-3-(4-methoxyphenyl)-5-(tert. butyldimethysilyloxy)-cyclopent-2-en-1-one.

13. A compound according to claim 1, having formula (53)

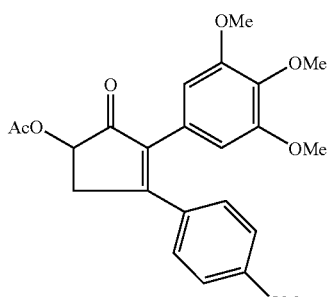

and is 2-(3,4,5-trimethoxyphenyl)-3-(4-methoxyphenyl)-5-acetoxy-cyclopent-2-en-1-one.

14. A compound according to claim 1, having formula (54)

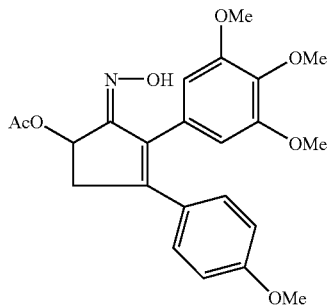

and is 2-(3,4,5-trimethoxyphenyl)-3-(4-methoxyphenyl)-5-acetoxy-cyclopent-2-en-1-one oxime.

15. A compound according to claim 1, having formula (55)

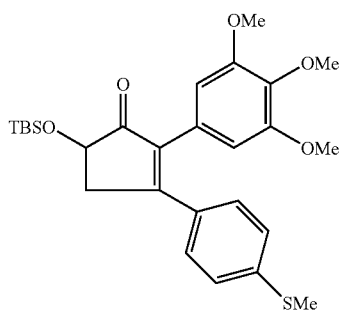

and is 2-(3,4,5-trimethoxyphenyl)-3-(4-methylsulphanylphenyl)-5-(tert. butyldimethysilyloxy)-cyclopent-2-en-1-one.

16. A compound according to claim 1, having formula (56)

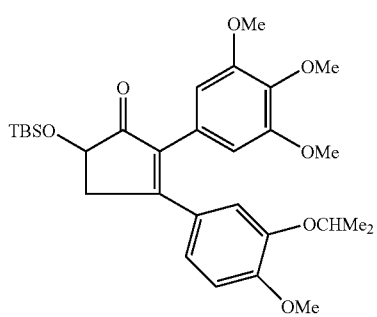

and is 2-(3,4,5-trimethoxyphenyl)-3-(3-isopropyloxy-4-methoxyphenyl)-5-(tert. butyldimethysilyloxy)-cyclopent-2-en-1-one.

17. A compound according to claim 1, having formula (59)

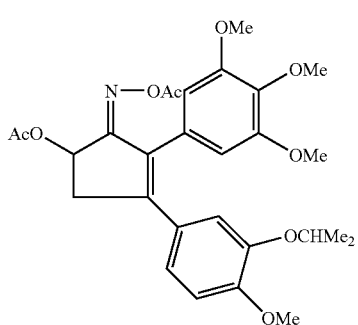

and is 2-(3,4,5-trimethoxyphenyl)-3-(3-isopropyloxy-4-methoxyphenyl)-5-acetoxycyclopent-2-en-1-one acetoxylimine.

18. A compound according to claim 1, having formula (60)

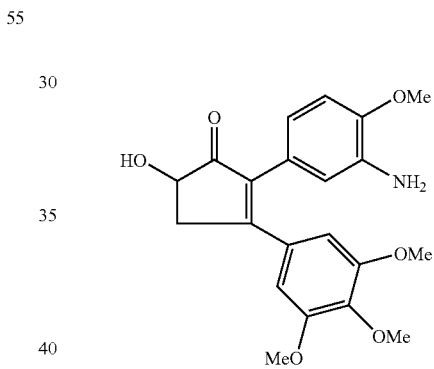

and is 2-(3-amino-4-methoxyphenyl-3-(3,4,5-trimethoxyphenyl)-5-hydroxycyclopent-2-en-1-one.

19. A compound according to claim 1, having formula (63)

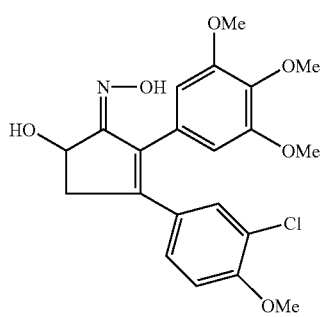

and is 2-(3,4,5-trimethoxyphenyl)-3-(3-chloro-4-methoxyphenyl)-5-hydroxycyclopent-2-en-1-one oxime.

20. A compound according to claim 1, having formula (64)

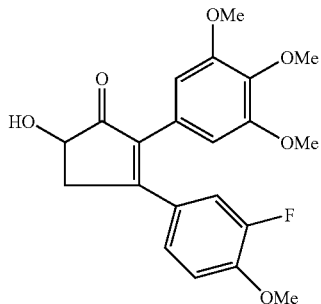

and is 2-(3,4,5-trimethoxyphenyl)-3-(3-fluoro-4-methoxyphenyl)-5-hydroxycyclopent-2-en-1-one.

21. A compound according to claim 1, having formula (65)

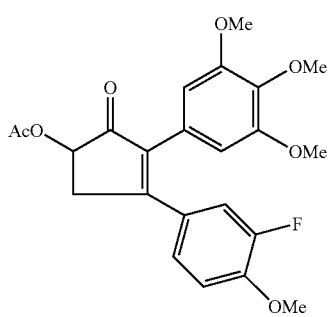

and is 2-(3,4,5-trimethoxyphenyl)-3-(3-fluoro-4-methoxyphenyl)-5-acetoxycyclopent-2-en-1-one.

22. A compound according to claim 1, having formula (66)

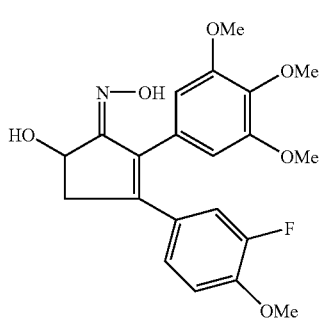

and is 2-(3,4,5-trimethoxyphenyl)-3-(3-fluoro-4-methoxyphenyl)-5-hydroxycyclopent-2-en-1-one oxime.

23. A compound according to claim 1, having formula (67)

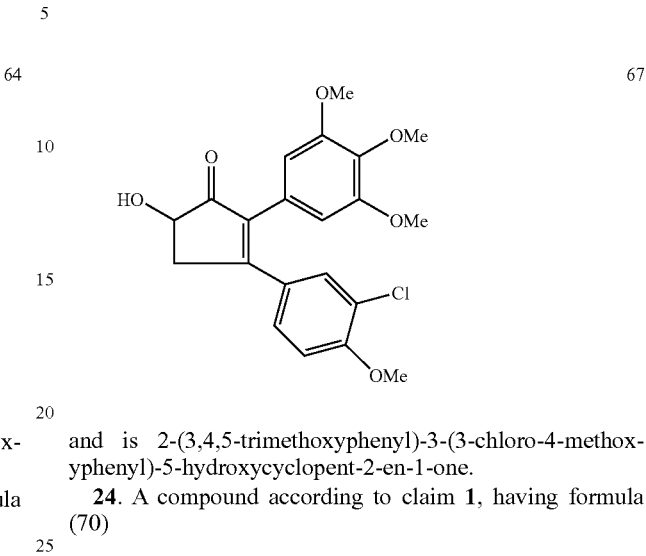

and is 2-(3,4,5-trimethoxyphenyl)-3-(3-chloro-4-methoxyphenyl)-5-hydroxycyclopent-2-en-1-one.

24. A compound according to claim 1, having formula (70)

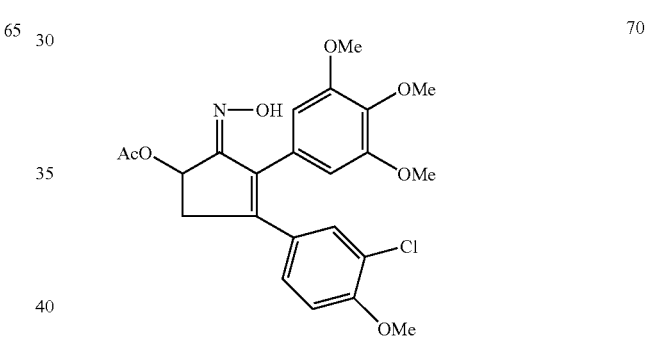

and is 2-(3,4,5-trimethoxyphenyl)-3-(3-chloro-4-methoxyphenyl)-5-acetoxycyclopent-2-en-1-one oxime.

25. A compound according to claim 1, having formula (71)

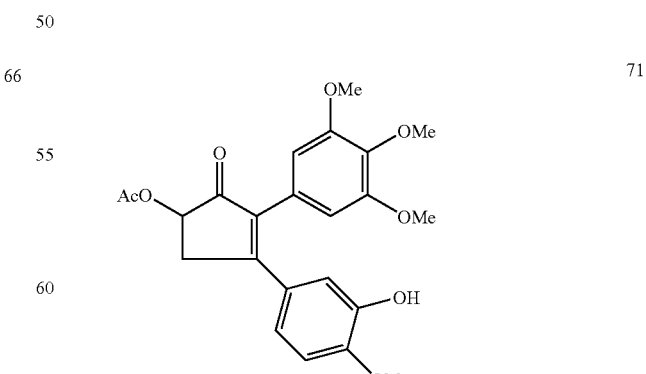

and is 2-(3,4,5-trimethoxyphenyl)-3-(3-hydroxy-4-methoxyphenyl)-5-acetoxycyclopent-2-en-1-one.

26. A compound according to claim 1, having formula (72)

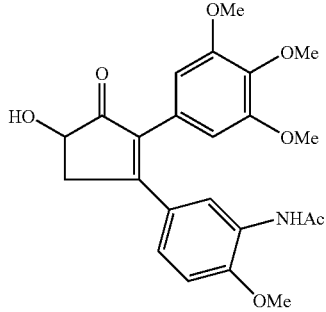

and is 2-(3,4,5-trimethoxyphenyl)-3-(3-acetamido-4-methoxyphenyl)-5-hydroxycyclopent-2-en-1-one.

27. A compound according to claim 1, having formula (73)

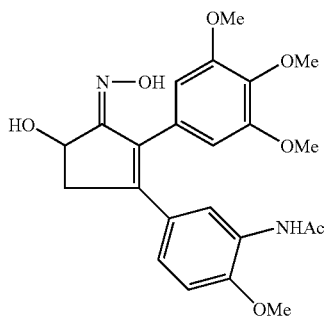

and is 2-(3,4,5-trimethoxyphenyl)-3-(3-acetamido-4-methoxyphenyl)-5-hydroxycyclopent-2-en-1-one oxime.

28. A compound according to claim 1, having formula (75)

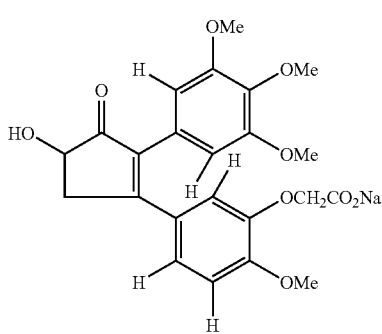

29. A compound according to claim 1, of the formula 1A

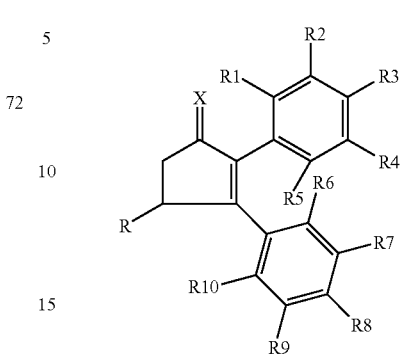

wherein $R_1$, $R_5$ and $R_{10}$ are hydrogen, R is OH, OTBS, OAc, O or N—OH; $R_2$ is OMe or H; $R_3$ is OMe or H; $R_4$ is OMe, H, or $NO_2$; $R_6$ is H or OMe: $R_7$ is H, Me, OMe, COOMe, OMOM, or OH; $R_8$ is OMe or H; $R_9$ is H, Me, or OMe; and X is O, or N—OH with the proviso that when $R_1$, $R_2$, $R_3$, $R_4$, $R_5$, $R_6$, $R_7$, $R_8$, $R_9$ and $R_{10}$ are hydrogen and X is oxygen, then R is not OH.

30. A compound according to claim 1, of the formula 1B

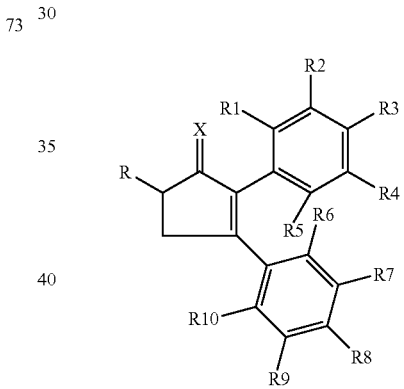

wherein $R_1$, $R_5$, $R_6$ and $R_{10}$ are hydrogen, R is OH, OTBS, or OAc; $R_2$ is $NO_2$, OMe or $NH_2$; $R_3$ is OMe; $R_4$ is H or OMe; $R_7$ is OMe, H, isopropyloxy, Cl, F, OH, NHAc or $OCH_2CO_2Na$; $R_8$ is OMe or SMe; $R_9$ is OMe or H, and X is O, N—OH, or NOAc.

31. A composition comprising a compound of any one of claims 1–30, and a pharmaceutically acceptable additive, diluent, excipient, solvent, binder, stabilizer, carrier, filler or lubricant.

32. A composition as claimed in claim 31, which provides 0.1 to 10 gram per unit dose of the compound of formula 1, a salt or derivative thereof.

33. The composition as claimed in claim 31, in the form of a tablet, lozenge, capsule, powder, aqueous or oily suspension, syrup, elixir, implant or aqueous solution.

34. A method for treating the growth of carcinoma of the colon, pancreas, larynx, ovary, duodenum, kidney, oral cavity, prostate, or lung, or endothelial cells or leukemia, comprising administering an effective amount of a compound of formula (1) as claimed in any one of the claims 1 to 30 to a patient in need thereof.

35. A method as claimed in claim 34, wherein said patient is a mammal.

36. The method as claimed in claim 34, wherein the dosage for humans is in the range of 1 mg/Kg. B. Wt to 300 mg/Kg. B. Wt.

37. The method as claimed in claim 34, wherein the compound is administered to the patient systemically.

38. A method for treating the growth of tubulin in a patient comprising administering an effective amount of a compound of formula (1) as claimed in any one of the claims 1 to 30 to the patient in need thereof.

39. A method for inducing the enzyme caspase-3 in a patient comprising administering an effective amount of a compound of formula (1) as claimed in any one of the claims 1 to 30 to the patient in need thereof.

40. A method for reducing the level of VEGF in a patient comprising administering an effective amount of a compound of formula (1) as claimed in any one of the claims 1 to 30 to the patient in need thereof.

41. The compound according to claim 1 wherein CONH-alkyl is a CONH—$(C_1$–$C_4)$alkyl group.

* * * * *